(12) United States Patent
Koashi

(10) Patent No.: US 6,791,075 B2
(45) Date of Patent: Sep. 14, 2004

(54) METHOD OF SPECTRUM ANALYSIS IN TWO-DIMENSIONAL REPRESENTATION

(76) Inventor: Katsue Koashi, C25-103, 2-7, Shinsenri, Higashi-machi, Toyonaka-shi, Osaka-fu (JP)

( * ) Notice: Subject to any disclaimer, the term of this patent is extended or adjusted under 35 U.S.C. 154(b) by 265 days.

(21) Appl. No.: 09/782,440

(22) Filed: Feb. 13, 2001

(65) Prior Publication Data

US 2001/0032923 A1 Oct. 25, 2001

(30) Foreign Application Priority Data

Mar. 24, 2000 (JP) .......................................... 2000-083319
Oct. 31, 2000 (JP) .......................................... 2000-332077

(51) Int. Cl.$^7$ ................................................. G01J 3/50
(52) U.S. Cl. ........................... 250/226; 702/40; 702/155
(58) Field of Search ........................... 250/226; 702/32, 702/40, 28, 155

(56) References Cited

U.S. PATENT DOCUMENTS 6,154,708 A * 11/2000 Koashi .......................... 702/40

OTHER PUBLICATIONS

Koashi, "Spectral Data Analysis by TwoDimensional Representation of Derivatives," *Applied Spectroscopy*, vol. 53, No. 6, pp. 701–712 (1999).

* cited by examiner

Primary Examiner—David V. Bruce
Assistant Examiner—Courtney Thomas
(74) Attorney, Agent, or Firm—Merchant & Gould, P.C.

(57) ABSTRACT

The present invention relates to a method for extracting individual band components from heavily overlapping bands. The method is based on first derivative-second derivative plots of an experimental spectrum and consists of two stases. The first stage is concerned with the geometric approach that estimates a set of values for the parameters of a component band in the overlapping bands, and repeats band decomposition of the remaining bands in the same manner after removing the estimated band from the overlapping bands. The second stage is to minimize the difference between the profiles of the estimated band and its complementary band by a least-squares optimization, and then to determine the optimum values of the band parameters.

6 Claims, 25 Drawing Sheets

METHOD OF SPECTRUM ANALYSIS IN TWO-DIMENSIONAL REPRESENTATION

FIELD OF THE INVENTION

The present invention relates to a method of spectrum analysis in two-dimensional representation to obtain accurate characteristic information on an object to be analyzed by using derivatives on spectral data of the said object in spectroscopic analysis.

DESCRIPTION OF THE PRIOR ART

Heretofore, in spectroscopic analysis (including infrared spectrophotometry and the like) in general, by measuring an intensity of light transmitting through the object to be analyzed(may hereafter be denoted as "analyzed object") and converting absorbance, various characteristics or information in terms of physical and/or chemical properties (may hereafter be denoted as "characteristic information") including shapes, concentration, and the like of substances contained in the said analyzed object have been obtained based on the shapes of the said spectrum or a spectral profile. As such a conventional spectral profile, that spectral profile representing absorbance of the analyzed object in terms of the wavenumber (or wavelength) are generally used (may hereafter be referred to as "absorbance/wavenumber spectral profile"). It can be considered that such a spectral profile is formed with a number of component bands overlapped.

As a means to analyze such spectral profiles, for example, the Japanese patent publication H11-148865 discloses the method of using derivatives on the spectral waveform of the analyzed object in spectroscopic analysis. To be concrete, as for the specific analyzed object, when spectral waveform where the intensity of the signal output of a spectrophotometer is represented as a function of wavenumber, wavelength, or time is prepared letting n1 and n2 (n1≠n2) be a positive integer, a method of spectrum analysis in two-dimensional representation with the following characteristics is disclosed. These characteristics are;

Calculating the n1-th and n2-th derivatives with respect to wavenumber, wavelength, or time of the said intensity of the signal output regarding the spectral profile on the said spectral data, plotting points on the two-dimensional coordinate plane whose X-coordinate is the said n1-th derivative and whose Y-coordinate is the said n2-th derivative, respectively, on the said two-dimensional coordinate plane, creating a two-dimensional plot of derivative pairs on the said spectral waveform, thereby obtaining specific information on the said spectral profile based on the two-dimensional plot of the said derivative pairs.

However, although the spectral analysis method cited in the Japanese patent publication H11-148865 can find component bands when the spectral profile contains a (single) component band, it is difficult to find all these component bands and even to estimate them is extremely difficult when the spectral profile of the analyzed object contains several component bands overlapped. In particular, there are many cases that the spectral profile of the analyzed object has several overlapping component bands. Therefore, as for the analyzed object with a spectral profile containing several component bands, the method described in the Japanese patent publication H11-148865 can estimate the dominant component bands to some extent among the said component bands. However, as for unresolved bands buried under the dominant band, that is, the characteristics of those component bands are unclear due to severe overlap, it is extremely difficult even to estimate those bands.

SUMMARY OF THE INVENTION

Based on the method cited in the Japanese patent publication H11-148865, the present invention has been developed for further improvement. As a result of intensive studies, as for the specific analyzed object, when spectral data where the intensity of the signal output of a spectrophotometer is represented as a function of wavenumber, wavelength, or time, are prepared letting n and m (n≠m) be a positive integer, the inventor has proposed a method of spectrum analysis in two-dimensional representation for obtaining the specific characteristic information on the said spectral data based on the said two-dimensional derivative plot by calculating the n-th and m-th derivatives with respect to wavenumber, wavelength, or time, of the said spectral data, plotting points on the two-dimensional coordinate plane as the X-Y coordinate system whose X-coordinate is the said n-th derivative and whose Y-coordinate is the said m-th derivative respectively on the said two-dimensional coordinate plane, and preparing the two-dimensional derivative plot on the said spectral data.

Further, based on the characteristic information described above, the inventor has proposed a method of spectrum analysis in two-dimensional representation which estimates the component bands comprising the spectral profile of the analyzed object by estimating band parameter values regarding at least one component band among the component bands contained in the spectral profile of the analyzed object, estimating at least one component band, obtaining the two-dimensional derivative plot with the specific remaining component bands removed by clearing the specific component band or specific component bands already estimated or the two-dimensional derivative plot from spectral profiles or the two-dimensional derivative plot of analyzed object, obtaining specific characteristic information based on the two-dimensional derivative plot of this specific component removed, estimating band parameter values on other component bands based on the said characteristic information, and iterating the estimation of at least one of the other component bands thereby estimating component bands in order.

That is, the present invention is a method of estimating component bands in order, using a specific component band or specific component bands already estimated and estimating remaining component bands (including the ones not yet estimated, the ones desired to be optimal).

To be concrete, a preferred embodiment of the present invention, although not specifically limited, is, first of all, to estimate one component band BDi(i is a positive integer) by estimating the band parameter values for BDi among component bands contained in the spectral profile of the analyzed object based on the specific characteristic information on the spectral profile of the two-dimensional derivative plot.

Next, the preferred embodiment is to prepare the two-dimensional derivative plot with BDi removed, either creating the two-dimensional derivative plot with BDi removed by clearing the two-dimensional derivative plot of the component band BDj (j is a positive integer where j≠i) from the two-dimensional derivative plot of the said analyzed object or obtaining the spectral profile with BDi removed by clearing a profile of BDi from a spectral profile of the said analyzed object.

Then, the preferred embodiment is to estimate one component band BDj by estimating band parameter values on BDj other than BDi among the component bands contained in the spectral profile of the analyzed object based on the said characteristic information by obtaining the specific characteristic information based on the said two-dimensional derivative plot with BDi removed.

Next, the preferred embodiment is to prepare a two-dimensional derivative plot with BDj removed, either creating the two-dimensional derivative plot with at least BDj removed by clearing BDj or the two-dimensional derivative plot of both BDi and BDj from the two-dimensional derivative plot of the said analyzed object or obtaining the spectral profile with at least BDj removed by clearing BDj or the profile of both BDi and BDj from a spectral profile of the said analyzed object.

Then, the preferred embodiment is to estimate the component band BDk (k is a positive integer where at least k≠j) by estimating band parameter values on BDk other than BDj among the component bands contained in the spectral profile of the analyzed object based on the said characteristic information by obtaining the specific characteristic information based on the said two-dimensional derivative plot with BDi removed.

Thus, the present invention is a procedure of estimating other component bands in order as for component band contained in the spectral profile of the analyzed object, using the specific component band or specific component bands already estimated by iterating estimation of component bands, creating the two-dimensional derivative plot with information on an estimated component band or estimated component band removed from the information on the analyzed object, acquiring the specific information based on this two-dimensional derivative plot and operating the estimation of other component bands based on this characteristic information.

In the two-dimensional derivative plot on spectral data of the analyzed object, the characteristic information on dominant component bands can be distinguished to some extent, however, as for characteristic information on unresolved component bands buried under the dominant component band, since it is subtle or since it overlaps with the characteristic information of other component bands overlapping with the said component band, the characteristic information of the said component band of its own becomes unclear and it is difficult to be distinguished.

Particularly, in the case where the overlapping component bands are dominant ones, the characteristic information on the unresolved component bands buried under the dominant component band can seldom be distinguished.

However, as the analytic method of the present invention shows, when the two-dimensional derivative plot is created by removing information on dominant component bands estimated from the characteristic information of the two-dimensional derivative plot of the analyzed object from the information about the analyzed object and by obtaining the two-dimensional derivative plot based on the spectral profile after removal of information on dominant component bands, the characteristic information of component bands hidden by overlapping dominant component bands appears, which enables to obtain the characteristic information about component bands hidden by overlapping, and further enables to obtain the characteristic information which has never been achieved by the two-dimensional derivative plot on the spectral data of the analyzed object.

Then, by iterating the operations of removing the profile of single or several component bands already estimated from the information about the analyzed object and by obtaining the characteristic information using the two-dimensional derivative plot based on the removal thereafter estimating other component bands, estimating the component band contained in the spectral profile of the analyzed object in order with suitability can be achieved.

Thus, the method of estimating a single component band or several component bands contained in the spectral profile of the analyzed object and finding the other component bands in order by using the two-dimensional derivative plot obtained by removing the profile of the single component band or several component bands from the spectral profile of the analyzed object, or this procedure is called "Band Stripping".

Therefore, when the method of the present invention is employed, the component band that is contained in the spectral profile of the analyzed object can be estimated easily.

Further, in the preferred embodiment of the present invention, the component band is a Gaussian band, a Lorentzian band, or the mixture thereof.

In the present invention, n is preferably 1 and/or 3 and m is n+1. When the combination of n and m is (n,m)=(1,2), (3,4), the characteristic information on the spectral data appears clearly. Therefore, when the two-dimensional derivative plot is created with the combination of (n,m)=(1, 2)and/or (3,4), the characteristic information can be obtained easily.

According to the method of spectrum analysis in two-dimensional representation, in the two-dimensional derivative plot where pairs of the first and second derivatives are represented in the X-Y coordinate system, when a typical local minimum indicates the existence of a corresponding component band, an X position of the said local minimum is a first approximation of band center position Xc of the said component band, setting several points on the said two-dimensional derivative plot in the vicinity of $P_d$, point of intersection of the said two-dimensional derivative plot with the X-axis, as candidates for the inflection point of the said component band, estimating the bandwidth of the said component band from the candidate of the said inflection point by the following Equation (1), estimating the peak height of the said component band from the distances between the said local minimum and the point(s) of intersection of vertical line passing through the said local minimum and the horizontal line(s) passing through the said candidate points, obtaining the candidates for band parameter values of the said component band, and further obtaining the constraint conditions subjected to the band parameter values for the said component band from the said two dimensional derivative plot, the relation between the bandwidth $b_w$ and the X-position of the inflection point $X_p$ of a single band can be preferably expressed by $$b_w = (1/Kp) |X_c - X_P| \tag{1}$$

(In Equation, $b_w$ is an estimated value of the bandwidth of a Gaussian or a Lorentzian band, where the coefficient $K_P$ is 0.42466 for Gaussian and 0.288675 for Lorentzian.)

According to the method of spectrum analysis in two-dimensional representation, in the two-dimensional derivative plot where pairs of the third and fourth derivatives are represented in the X-Y coordinate system, when a typical local maximum indicates the existence of a corresponding component band, an X position of the said local maximum is a first approximation of band center position $X_c$ of the said component band, setting several points on the said two-dimensional derivative plot in the vicinity of $Q_d$, point of intersection of the said two-dimensional derivative plot with the X-axis, as candidates for the secondary inflection point of the said component band, estimating the bandwidth of the said component band from the candidate of the said secondary inflection point by the following Equation (2), estimating the peak height of the said component band from the distances between the said local maximum and the point(s) of intersection of vertical line passing through the said local maximum and the horizontal line(s) passing through the said candidate points, obtaining the candidates for band parameter values of the said component band, and further obtaining the constraint conditions subjected to the band parameter values for the said component band from the said two dimensional derivative plot, the relation between the bandwidth $b_w$ and the X-position of the secondary inflection point $X_Q$ of a single band can be preferably expressed by $$b_w = (1/K_P) |X_c - X_Q| \quad (2)$$

(In the Equation, $b_w$ is an estimated value of the bandwidth of a Gaussian or a Lorentzian band, where the coefficient $K_Q$ is 0.31508 for Gaussian and 0.16426 for Lorentzian.)

In the present invention, the method of spectral analysis in two-dimensional representation which adjusts the already estimated band parameter values can preferably be used so that the specific component band already estimated and the complementary estimated component band with all the estimated component bands other than the said estimated specific component band removed from the spectral profile of the analyzed object or two-dimensional derivative plot coincide.

With the said band stripping method, the parameter values of the each component band cannot be truly estimated and it sometimes fails into a so-called local optimum. This is because the adjacent component bands overlap and when the parameter values of the specific component band are too large or too small, the overestimation and/or underestimation affect(s) the parameter values such as band center position, bandwidth, and peak height of the adjacent component bands. Therefore, the present invention is capable of estimating the band parameter values for the component band with further suitability by introducing "complementary estimated component band".

The example of the coincidence between the specific estimated component band (denoted as eBD) and its complementary estimated component band (cBD) includes a method of minimizing the total sum of the distance of the iso-wavenumber lines between eBD and cBD in the two-dimensional derivative plots. By adjusting the parameter values for the specific estimated component band and by minimizing the difference between eBD and cBD, the estimated parameter values become as close to the true value as possible. In addition, by improving the degree of symmetry of the complementary estimated component band, the adjacent band parameter values are optimized. In other words, by adjusting the band parameter values for the specific estimated component band, the degree of symmetry of the complementary estimated component band is improved. Thus, introducing the complementary estimated component band and aiming to optimize the estimated band parameter values already obtained is called "Complementary Matching" method.

The object of the present invention is to provide a method of spectrum analysis that can easily estimate its several component bands of the analyzed object having spectral profile containing several component bands. In addition, it can be applicable to spectral data such as infrared spectra, visible light spectra, ultraviolet spectra, Raman spectra, X-ray diffractogram, and chromatogram, and the like.

DESCRIPTION OF THE PREFERRED EMBODIMENT

Figure 1:
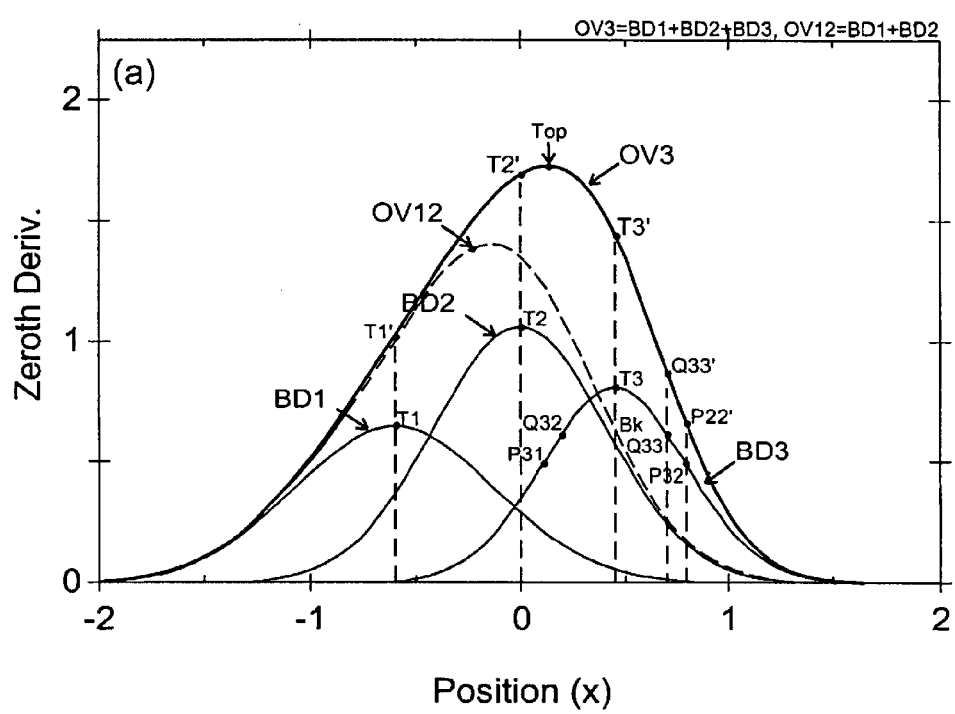
FIG. 1 is a graph depicting an original spectrum having three component bands overlapped.

The present invention is explained in detail based on the drawings. FIG. 1 shows the original spectrum generated (or synthesized) that is consisted of the three overlapping component bands. The explanation goes as for a method of estimating component band from these graphs.

As a shape of the component band estimated by the spectral analysis method of the present invention, a Gaussian band, a Lorentzian band, or a mixture thereof can be considered.

A Gaussian band is expressed by the following Equation:

$$BD_G(X) = ph_G \exp\{-4 \log 2 \, (X-bc_G)^2/bw_G^2\} \quad (3)$$

(in the Equation, $bc_G$ is the center position of the band, $ph_g$ the peak height, and $bw_{G2}$ the bandwidth.)

A Lorentzian band is expressed by the following Equation:

$$BD_L(X) = ph_L/\{1 + 4(X-bc_L)^2/bw_L^2\} \quad (4)$$

(in the Equation, $bc_L$ is the center position of the band, $ph_L$ the peak height, and $bw_L$ the bandwidth.)

A mixture of a Gaussian and a Lorentzian band is expressed by the following Equation:

$$BD_m(X) = mBD_G(X) + (1-m)BD_L(X) \quad (5)$$

(in the Equation, $BD_G(X)$ is the Gaussian band given by Equation (3), $BD_L(X)$ the Lorentzian band given by Equation (4), and m is the ratio of the mixture where $0 < m < 1$.)

Further, the bandwidth is the full-width at half-height of the band (FWHH). In other words, the bandwidth is the distance between the two X positions at half-height of the band.

In the present invention, in order to find one component band which is contained in the original spectrum, the characteristic information is so obtained as by differentiating the original spectrum. "n-th-m-th two-dimensional derivative spectral profile" is so defined as the one with the n-th derivative on the X-axis and the m-th derivative on the Y-axis. In some cases, it is abbreviated as "Dn-Dm plot".

FIG. 1 shows the original spectrum of $OV_3$ (= $BD_1 + BD_2 + BD_3$) having $BD_1$, $BD_2$, and $BD_3$, three Gaussian component bands overlapped and spectral profile of each component band. That is, $OV_3$ is obtained by summing the component bands calculated by the following Equation (6).

$$BD_i(X) = ph_i \exp\{-4 \log 2 (X-bc_i)^2/bw_i^2\} \quad (6)$$

(in the Equation, i is 1, 2 or 3, representing the i-th band, $bc_i$ the center position of the band, $ph_i$ the peak height, and $bw_i$ the bandwidth.)

Spectral analysis is performed with Mathematica, mathematical software packages (ver.2.2, Wolfram Research, Inc., Illinois). The band parameter values for the individual component band are given as follows:

Component band $BD_1$:
$bc_1 = -0.5978$
$bw_1 = 1.1070$
$ph_1 = 0.6504$

Component band $BD_2$:
$bc_2 = 0.0012$
$Bw_2 = 0.9643$
$ph_2 = 1.0630$

Component band $BD_3$:
$bc_3 = 0.4533$
$Bw_3 = 0.8078$
$ph_3 = 0.8123$

In the simulation study estimating the component band, the parameter values are treated as unknown, however, the true parameter values described above are sometimes utilized in the course of the following explanation for evaluation of obtained results.

Mathematica is also used for calculations and drawings. In differential operation, analytic differentiation is performed and digitized with an interval of 0.01 so as to avoid the error caused by digital differentiation.

Here, in the usual spectral profile, the X-coordinate represents wavenumber, wavelength, or time, whereas the Y-coordinate represents absorbance. For convenience, the explanation goes defining that the X-coordinate represents wavenumber and the Y-coordinate represents absorbance.

Further, the range of the X-coordinate is $-2 \leq x \leq 2$. Here, in this specification, "the n-th derivative spectrum" is denoted as the derivative spectrum with the quantity of the Y-axis differentiated the n-th with respect to the X-axis. In addition, "two-dimensional derivative plot" is denoted as the derivative plot with the n-th derivative on at least one axis of the two axes in the two-dimensional coordinate plane as the X-Y coordinate system.

In the analytical procedure of the method of this invention, first, a two-dimensional plot of the analyzing spectrum is created, and band parameter values for at least one component band within the two-dimensional plot are estimated after obtaining the characteristic information. For this purpose, the characteristics of the component band are explained as below.

(Characteristic points of the component band)

In FIG. 1, among the three component bands, the characteristic points are shown as for the sharpest (with the narrowest bandwidth) component band $BD_3$. Point $T_3$ ($X_{T3} = 0.4533$) is the vertex. ($X_{T3}$ represents the X position of the point $T_3$ and the same representation follows hereafter.) Points $P_{31}$ ($X_{P31} = 0.1103$) and $P_{32}$ ($X_{P32} = 0.7963$) are the zero-crossing points of the second derivative and the inflection points. Points $Q_{32}$ ($X_{Q32} = 0.1988$) and $Q_{33}$ ($X_{Q33} = 0.7078$) are the innermost zero-crossing points of the fourth derivative and the inflection points. Hereafter, the innermost zero-crossing points of the fourth derivative are called secondary inflection points.

In estimating the parameter values for component band $BD_3$, band center position $bc_3$ can be estimated by the corresponding local minimum or maximum, and bandwidth $b_{W3}$ can be estimated by the following Equation. However, peak height $ph_3$ cannot be estimated easily. When point $B_K$ is so placed as the point where $X = X_{T3}$ on $OV_{12}$ which is obtained by removing $BD_3$ from $OV_3$, and when point $T_3'$ is so placed as the point where $X = X_{T3}$ on $OV_3$, the length of line segment $T_3 \cdot B_K$ corresponds to peak height $ph_3$. Therefore, if the X position of point $B_k$ can be estimated, peak height $ph_3$ can also be estimated.

Bandwidth $bw_i$ of component band $BD_i$ can be calculated from $X_{Pi1}$, the X position at inflection point $P_{i1}$, or from $X_{Pi2}$, the X position at inflection point $P_{i2}$, by the following Equations:

$$b_{Wi} = (1/K_P) |b_{Ci} - x_{pi1}| \quad (7)$$

$$b_{Wi} = (1/K_P) |b_{Ci} - x_{pi2}| \quad (8)$$

($K_P = 0.4247$ in the case of a Gaussian band, whereas $K_P = 0.2887$ in the case of a Lorentzian band.)

Bandwidth $b_{Wi}$ of component band $BD_i$ can be calculated from $X_{Qi2}$, the X position at the secondary inflection point $Q_{i2}$, or from $X_{Qi3}$, the X position at secondary inflection point $Q_{i3}$, by the following Equations:

$$b_{Wi} = (1/K_Q) |b_{Ci} - x_{Qi1}| \quad (9)$$

$$b_{Wi} = (1/K_Q) |b_{Ci} - x_{Qi2}| \quad (10)$$

($K_Q = 0.3151$ in the case of a Gaussian band, whereas $K_Q = 0.1625$ in the case of a Lorenztian band.)

In order to estimate each component band, it is necessary to find a typical local minimum, local maximum, and the inflection points of the corresponding component band on $OV_3$ where all component bands overlap. For this purpose, first, the feature of $OV_3$ is studied by means of its derivative.

Figure 2:
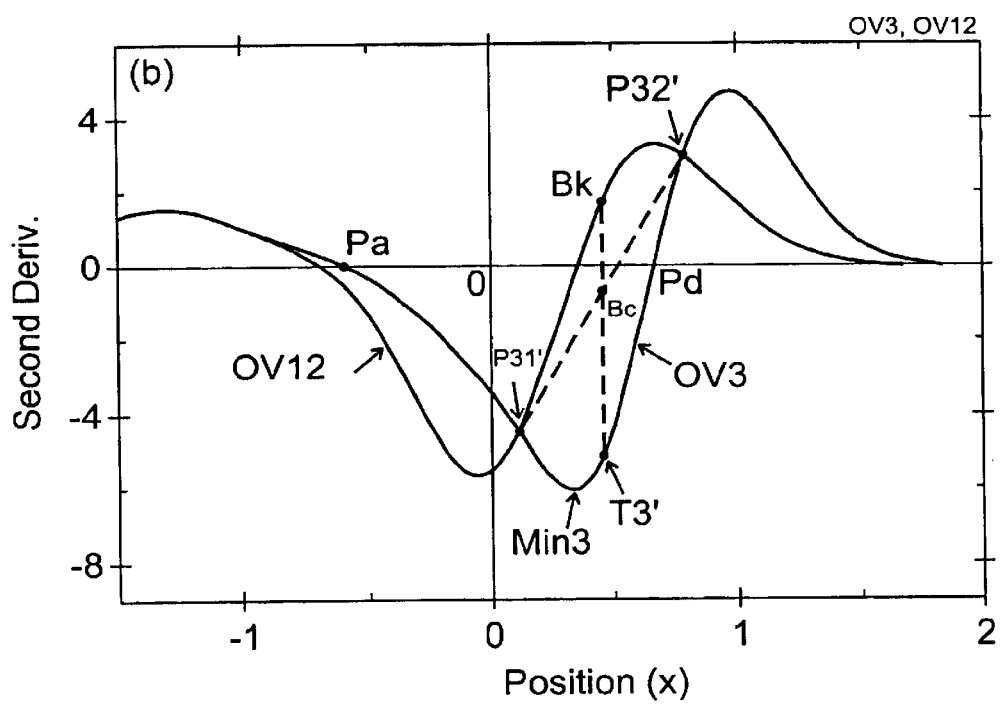
FIG. 2 is a graph depicting a second derivative spectrum of the original one shown in FIG. 1.
Figure 3:
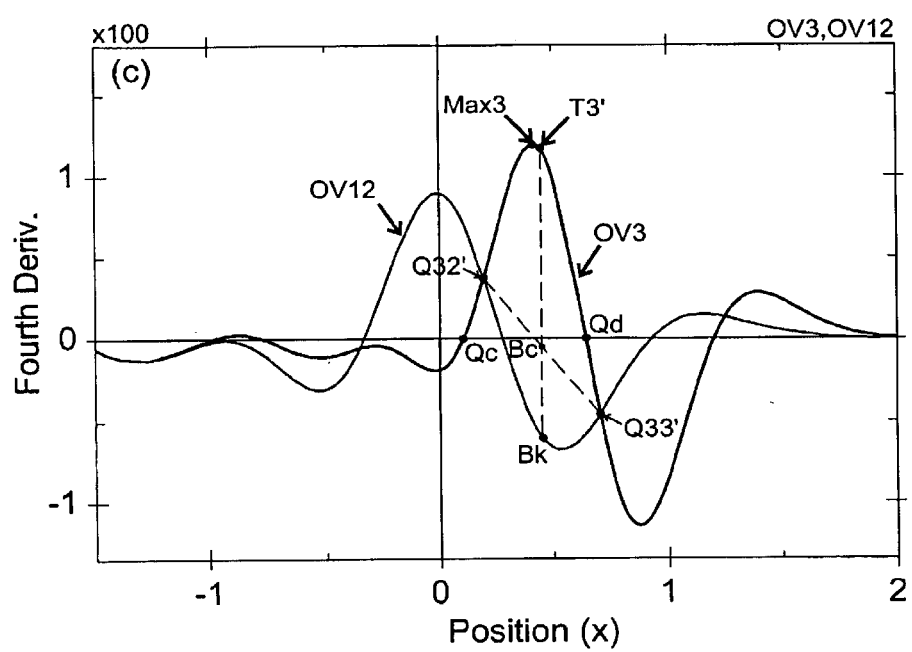
FIG. 3 is a graph depicting a fourth derivative spectrum of the original one shown in FIG. 1.

The second derivative spectrum of the original one in FIG. 1 is shown in FIG. 2, while the fourth derivative spectrum in FIG. 1 is shown in FIG. 3. $OV_{12}$ is the spectrum where $BD_3$ is subtracted from $OV_3$ (i.e., $OV_{12}=OV_3-BD_3$) or the spectrum where $BD_1$ and $BD_2$ overlap (i.e., $OV_{12}=BD_1+BD_2$). In FIG. 2, Min3 is the local minimum, points $P_d$ and $P_d$ are the inflection points of $OV_3$.

Points $P_{31}'$ and $P_{32}'$ correspond to inflection points $P_{31}$ and $P_{32}$ of $BD_3$ and they are the isosbestic points in the second derivative. As in the initial spectral profile, the length of line segment $T_3'BK$ corresponds to the peak height of $BD_3$. It should be noted that a peak height of a differential spectrum does not equal that of an original spectrum, and it should be calculated based on a peak height at the second-order differentiation of a Gaussian band with a unit peak height ($ph_t=1$) having the same bandwidth.

In the fourth derivative in FIG. 3, Max3 is the local maximum, and points $Q_c$ and $Q_d$ are the inflection points of the second derivative of $OV_3$. Points $Q_{32}'$ and $Q_{33}'$ correspond to secondary inflection points $Q_{32}$ and $Q_{33}$ of $BD_3$ and they are the isosbestic points in the fourth derivative. The length of segment $T_3'BK$ corresponds to the peak height of $BD_3$.

It should be noted that Min3 is the local minimum of the second derivative spectrum of $OV_3$, and Max3 is the local maximum of the fourth derivative spectrum of $OV_3$. A typical local minimum or local maximum indicates that a corresponding component band exists in the vicinity thereof. According to the illustration of FIG. 2, only Min3 is the local minimum of the second derivative spectrum of $OV_3$ and there is no local minimum that corresponds to other component bands $BD_1$ and $BD_2$. On the other hand, according to the illustration of FIG. 3, the typical Max3 exists as the local maximum of the fourth derivative spectrum of $OV_3$. Further, although there are other two local maxima, since they are modulated by the side lobe of the dominant peak, it is not clear whether they indicate the existence of the corresponding component bands.

From the description mentioned above, $BD_3$ is the analyzing component in which the local minimum is typically at the second derivative spectrum and in which the local maximum is typically at the fourth derivative and the remaining components $OV_{12}$ is called "background components". Then, estimating band parameter values is examined based on the algebraic geometry. In a spectrum where many component bands overlap, the generalization is possible by regarding it as the two-component system of the "analyzing" component band and the "background" components. "Two-dimensional derivative plot" refers to plotting the pairs of the n-th and m-th derivatives in the two-dimensional coordinate. It can be abbreviated as "Dn-Dm" plots.

Figure 4:
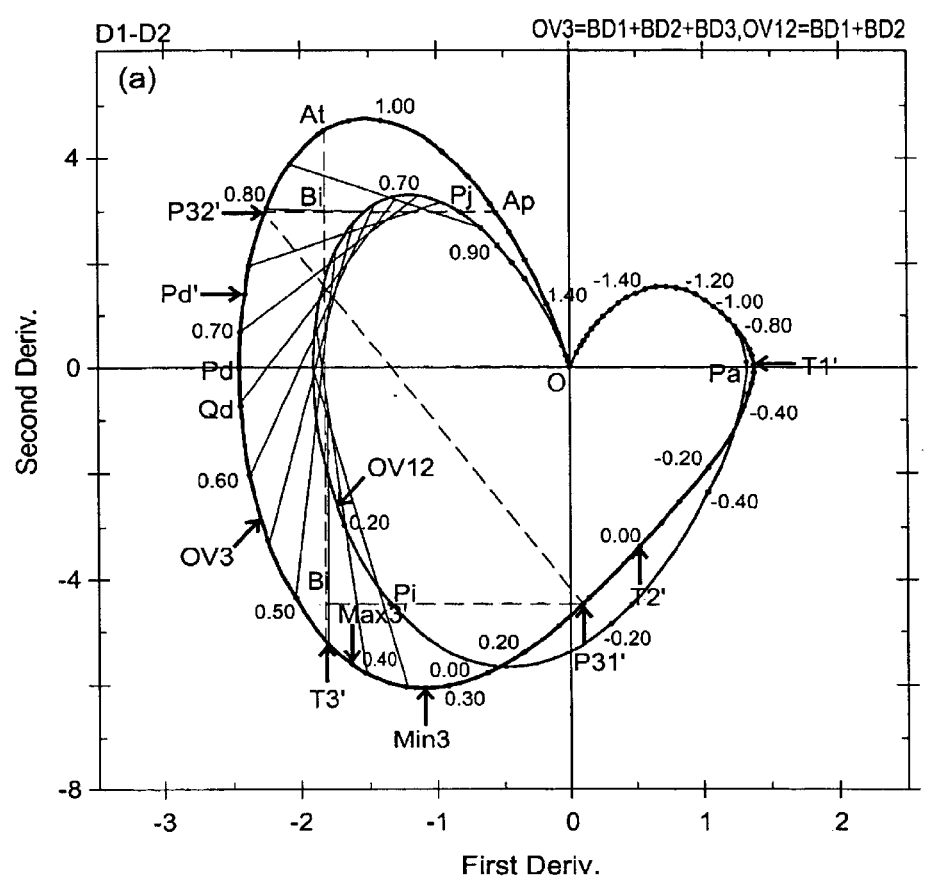
FIG. 4 is D1–D2 plots for $OV_3$ and $OV_{12}$.

D1–D2 plots are shown in FIG. 4, in the two-dimensional representation of the pairs of the first derivative and the second derivative. D3–D4 plots are shown in FIG. 5, in two-dimensional representation of the pairs of the third derivative and the fourth derivative.

Letters and sequential numbers are attached as for the characteristic points of the corresponding component band $BD_3$.

Figure 5:
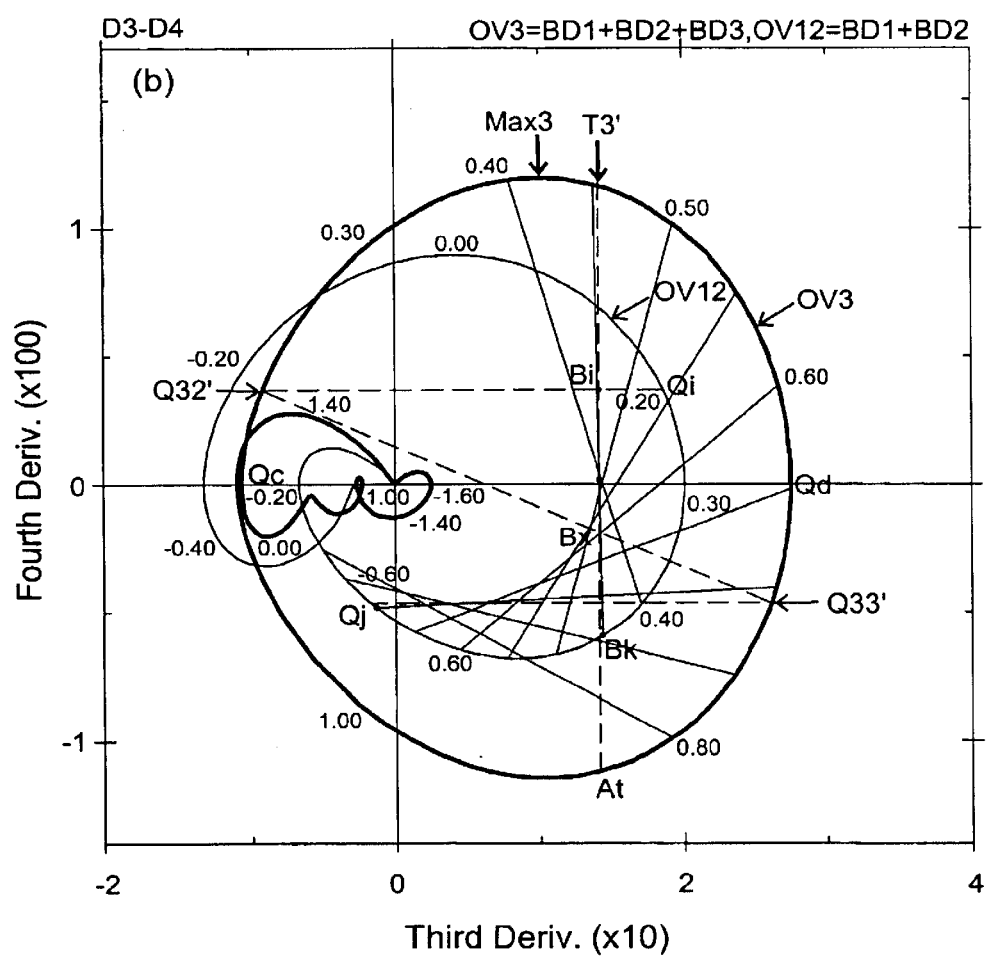
FIG. 5 is D3–D4 plots for $OV_3$ and $OV_{12}$.

That is, in FIGS. 4 and 5, points $T_3'$, $P_{31}'$, $P_{32}'$, $Q_{32}'$, and $Q_{33}'$ on $OV_3$ correspond to points $T_3$, $P_{31}$, $P_{32}$, $Q_{32}$, and $Q_{33}$ on $BD_3$, respectively.

In D1–D2 plots in FIG. 4, if the position of $T_3'$, $P_{31}'$, or $P_{32}'$ can be estimated, or in D3–D4 plots in FIG. 5, if the position of $T_3'$, $Q_{32}'$, or $Q_{33}'$ can be estimated, the band center position of $BD_3$ and its bandwidth can be determined by Equation (3) or (4).

In D1–D2 plots in FIG. 4, the local minimum Min3 can be a candidate for $T_3'$, and the point of intersection of D1-axis, $P_d$, can be a candidate for $P_{32}'$. However, it should be noted that the X position of Min3 ($X_{min3}=0.3285$) is away from that of point $T_3'$ ($X_{T3}=0.4533$), the true value, and the X position of point $P_d$ ($X_{Pd}=0.6746$) is far away from that of point $P_{32}'$ ($X_{P32}=0.7963$).

On the other hand, in D3–D4 plots in FIG. 5, the local maximum Max3 can be a candidate for $T_3'$, and $Q_d$, the point of intersection of $D_3$-axis can be a candidate for $Q_{33}'$. X position of Max3 ($X_{max3}=0.4180$) is closer to that of point $T_3'$. Further, X position of point $Q_d$ ($X_{Qd}=0.6482$) is closer to that of point $Q_{33}'$ ($X_{Q33}=0.7078$), the true value. Concerning the two-dimensional derivative plot, since D1–D2 plots have simpler shapes than do D3–D4 plots, the explanation goes transferring the characteristic points on D3–D4 plots to those of D1–D2 plots, where the point corresponding to Max3 is denoted Max3' and the inflection point converted by the secondary inflection point $Q_d$ is denoted $P_d'$.

Iso-wavenumber lines are used for explaining the geometrical relation of the characteristic points on the two-dimensional derivative plot. Iso-wavenumber lines are the straight lines connecting the same wavenumber points between two spectra. In FIGS. 4 and 5, since it is complicated to draw the lines over entire range, the iso-wavenumber lines are drawn only in the region of interest. Here, the sequence numbers along the profile represent the wavenumbers.

In FIG. 4, the iso-wavenumber lines passing through point $T_3'$ is parallel to $D_2$-axis. Let the point of intersection with $OV_{12}$ be point $B_k$, let the point of intersection of the extended iso-wavenumber line and $OV_3$ be point $A_t$. The length of line segment $T_3'B_k$ corresponds to the peak height of $BD_3$.

On the other hand, the iso-wavenumber lines passing through the inflection points $P_{32}'$ and $P_{31}'$, respectively, are parallel to D1-axis. Let the point of intersection of the iso-wavenumber lines passing through point $P_{32}'$ and $OV_{12}$ be point $P_j$, and let the point of intersection of the extended iso-wavenumber line with respect to $P_{32}'$ and $OV_{12}$ be point $A_p$. Let the point of intersection of the iso-wavenumber line passing through point $P_{31}'$ and $OV_{12}$ be point $P_i$. The length of line segment $P_{32}'P_j$ equals the length of line segment $P_{31}'P_i$, which corresponds to a half of the bandwidth between two inflection points of $BD_3$. Let the point of intersection of lines $T_3'B_k$ and $P_{32}'P_j$ be point $B_j$, and let the point of intersection of lines $T_3'B_k$ and $P_{32}'P_i$ be point $B_i$. Further, let the point of intersection of lines $T_3'B_k$ and $P_{31}'P_{32}'$ be point $B_x$.

According to FIG. 4, since points $B_k$ and $B_x$ are above the line which is parallel to D1-axis passing through point $P_d$ and are close to each other, it causes no problem when point $B_k$ is replaced by point $B_x$. In general, the position of point $B_k$ depends on the shape of background component $OV_{12}$ and it is difficult to find its position by the algebraic geometrical method.

Nevertheless, the permissible region of point $B_k$ can approximately be determined. When the component bands are close to each other, the shape of $OV_3$ is like that of a single band. At this time, the position of point $B_k$ is below that of point $B_x$, located in the vicinity of point $B_i$. Conversely, as the separation between the component bands is large, the position of point $B_k$ moves upward to that of point $B_x$. Further, when the separation between the component band becomes larger, another local minimum appears on $OV_3$ and the position of point $B_k$ is located in the vicinity of point $B_j$ which is above point $B_x$.

On the other hand, as for line segment $P_{32}'P_j$ corresponding to a half of the bandwidth between two inflection points of BD$_3$, point P$_j$ exists in the left-hand side of point A$_p$. That is, line segment P$_{32}$'P$_j$ is shorter than line segment P$_{32}$'A$_p$. Likewise, the same analysis can be applied to D3–D4 plot in FIG. 5. Based on the geometrical study described above, how to find estimated parameter values of a component band is explained one by one.

(Step 1)

As can be seen from FIG. 4, the X position of Max3' (or Min3) is the first approximation of band center position X$_c$ for the corresponding component band BD$_3$. Hereafter this point is denoted as eT$_3$. Draw a straight line L1 parallel to D1-axis passing through point eT$_3$. An estimated point eP$_{32}$, on OV$_3$, for the inflection point P$_{32}$ of BD$_3$ is placed in the vicinity of the inflection point P$_d$ of OV$_3$. In more detail, the X position of eP$_{32}$ is at the positive side of that of point P$_d$. Then, an estimated value of the bandwidth of BD$_3$ is calculated by Equation (8). Draw a straight line L2 parallel to D2-axis passing through point eP$_{32}$. Line L2 intersects line L1 at point B$_j$.

Next, an estimated point eP$_{31}$, on OV$_3$, for another inflection point of BD$_3$ is placed at the opposite side of point eP$_{32}$ with respect to point eT$_3$. Both points eP$_{31}$ and eP$_{32}$ are equidistant from point eT$_3$ with respect to the X-coordinate or the wavenumber. Line segment eP$_{32}$ eP$_{31}$ intersects line L1 at point B$_k$. From the length of line segment eT$_3$B$_j$ or eT$_3$B$_k$, an estimated value of the peak height of BD$_3$ is calculated.

Thus, a set of estimated values of band center position eBC$_3$, bandwidth eBW$_3$, and peak height ePH$_3$ for BD$_3$ can be obtained. In order to obtain the true values or optimal estimated values for BD$_3$, a candidate can be created by finding sets of parameter values on several sequential points as the estimated value of eP$_{32}$ from the vicinity of point P$_d$.

It is clear that when an estimated value of band center position eT3 is close to point T$_3$', a better estimated value of a bandwidth can be obtained. Table 1 shows the sets of estimated values of the bandwidth and the peak height for BD$_3$ calculated by using systematic sequential points for eP$_{32}$ when point eT$_3$ is equal to the true target point T$_3$'. eBW$_3$ is the estimated bandwidth, ePH3A is the peak height obtained by line segment eT$_3$B$_j$, and ePH3B is the peak height obtained by line segment eT$_3$B$_x$.

TABLE 1

| Set of estimated value | X coordinate of eP32 | eBW$_3$ | ePH3A | ePH3B |
|---|---|---|---|---|
| EstBD3a | 0.70 | 0.581 | 0.357 | 0.244 |
| EstBD3b | 0.71 | 0.604 | 0.404 | 0.283 |
| EstBD3c | 0.72 | 0.628 | 0.455 | 0.325 |
| EstBD3d | 0.73 | 0.652 | 0.509 | 0.372 |
| EstBD3e | 0.74 | 0.675 | 0.566 | 0.423 |
| EstBD3f | 0.75 | 0.699 | 0.628 | 0.478 |
| EstBD3g | 0.76 | 0.722 | 0.693 | 0.537 |
| EstBD3h | 0.77 | 0.746 | 0.761 | 0.602 |
| EstBD3i | 0.78 | 0.769 | 0.833 | 0.671 |
| EstBD3j | 0.79 | 0.793 | 0.908 | 0.744 |
| EstBD3k | 0.80 | 0.816 | 0.986 | 0.823 |
| EstBD3l | 0.81 | 0.840 | 1.07 | 0.907 |
| EstBD3m | 0.82 | 0.863 | 1.15 | 0.995 |
| EstBD3n | 0.83 | 0.887 | 1.24 | 1.09 |

Figure 6:
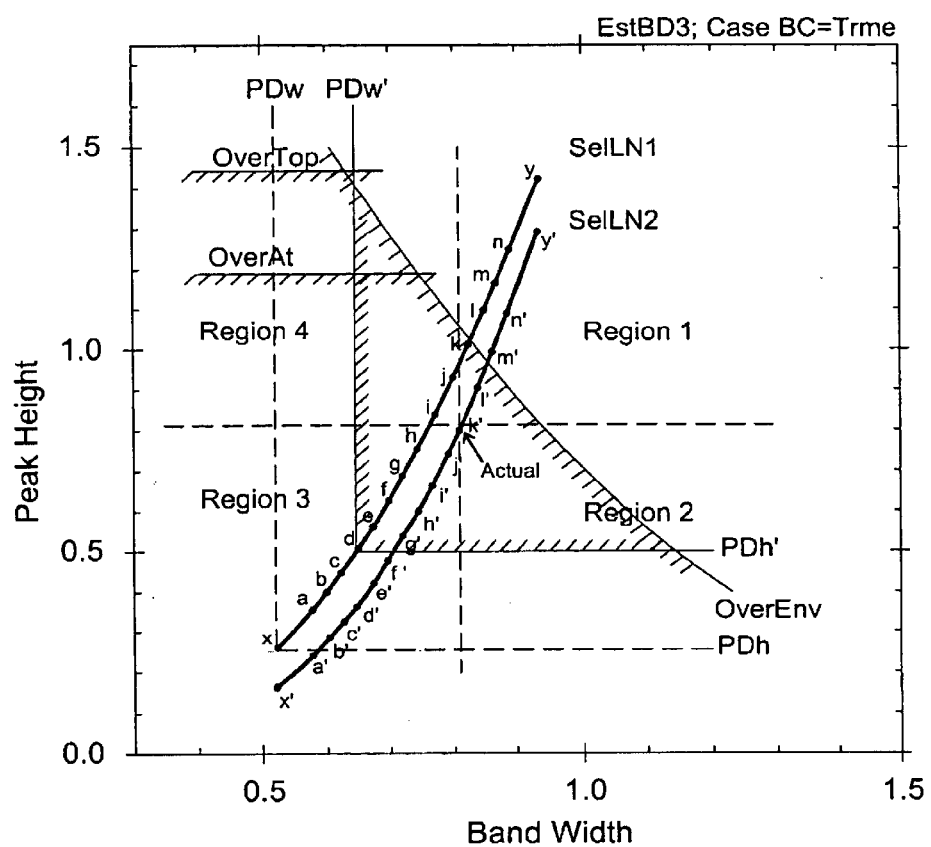
FIG. 6 is a graph showing the permissible range of the bandwidth and peak height for $BD_3$ estimation.

FIG. 6 shows the plots of the candidates of estimated values listed in Table 1 with a bandwidth at the Horizontal axis and with a peak height at the Vertical axis. Points a, b, c, . . . , n on the curve xy (this is called SelLN1) are calculated when peak heights are estimated by the length of line segment eT$_3$B$_j$ and sequence a', b', c', . . . , n' on the curve x'y' (this is called SelLN2) are calculated when peak heights are estimated by the length of line segment eT$_3$B$_x$.

The point indicated as 'actual' is the true point for BD$_3$. It is necessary to restrict estimated values from the algebraic geometrical constraint conditions.

According to FIG. 6, the constraint conditions subjected to the estimated values (set of the bandwidth and the peak height) are explained as below. As clearly shown in the spectral profile of FIG. 1, since BD$_3$ must be downward of OV$_3$, it must be BD$_3$(X)<OV$_3$(X). Since BD$_3$ must not exceed OV$_3$ at the estimated point of eT3, the band center position of BD$_3$, it must be BD$_3$(eT$_3$)<OV$_3$(eT$_3$). There is the upper limit for the peak height. That is, in FIG. 6, estimated values must lie below the straight line shown as 'OverTop'.

In addition, estimated values must be at the left-hand side of the curved line denoted as 'OverEnv'. When the bandwidth is small, a certain degree of the peak height is permissible, however, when the bandwidth is large, only a relatively small range of the peak height is permissible. Therefore, as shown in FIG. 6, qualitatively, OverEnv is the declined curved line from left to right.

Further, from D1–D2 plots shown in FIG. 4, the constraint conditions subjected to the estimated values can be calculated. From FIG. 4, the position in which the inflection point P$_{32}$' of BD$_3$ will exist must be above point P$_d$, the inflection point of OV$_3$. The inflection point for an estimated component band is above point P$_d$, which means that the bandwidth of the estimated component band is larger than that calculated from point P$_d$. Correspondingly, this means that the estimated value must be located at the right-hand side of line PD$_w$ in FIG. 6. In addition, likewise, since the points B$_j$ and B$_x$ are above point P$_d$, line segment eT$_3$B$_j$ or eT$_3$B$_x$ ought to be longer than the distance of eT$_3$ from the X-axis. Correspondingly, therefore, in FIG. 6, estimated values must be above line PDh.

Since point P$_d$' in FIG. 4 which corresponds to inflection point Q$_d$ in FIG. 5 has an effect of higher order derivatives, it is clear to be generally closer to point P$_{32}$'. Therefore, likewise, in FIG. 6, the estimated values must be located above line PDh' and right-hand side of line PDw'. In addition, from point A$_t$ which was already described, constraint of the peak height is introduced, which means in FIG. 6 that the estimated values are located below straight line OverA$_t$. Therefore, the constraint conditions subjected to a bandwidth and a peak height or permissible range thereof, are within the region of the hatched polygon bounded by straight lines PDw', PDh', OverEnv, and OverA$_t$.

Which point should be selected as the estimated values from selection line SelLN1 or SelLN2 is explained below. At x' end side of SelLN2, both the bandwidth and the peak height are smaller than the true value. Conversely, since y' end side of SelLN2, both the bandwidth and the peak height are larger than the true value and they exceed the curved line OverEnv. Points j', k', and l' in the vicinity of the middle part of SelLN1 are located close to the true value for BD$_3$. The upper limit of the bandwidth using point A$_p$ (the length of line segment P$_{32}$'P$_j$ corresponding to a half of the bandwidth of BD$_3$ is smaller than that of line segment P$_{32}$'A$_p$) is in the middle of points k' and l'. The position of the true value for BD$_3$ is around the center of the hatched triangle region shown in FIG. 6 when the degree of overlapping among the component bands is high. And the position of the true value for BD$_3$ is around the curved line OverEnv when the degree of overlapping is low. Around point k' is a good candidate as the estimated values for eBW$_3$ and ePH$_3$.

The procedure of finding estimated values for BD$_3$ was explained as mentioned above, assuming that the estimated value of the band center position is the true one. In general, the estimated value of band center $b_{c3}$ of component band $BD_3$ is selected as Max3' ($X_{max3}$=0.418).

Then, finding a set of a series of estimated values $eBD_3$, estimated values for $BD_3$ are selected. At this stage, a set of estimated values for $BD_3$ is obtained ($eBC_3$=0.418, $eBW_3$= 0.830, and $ePH_3$=0.780):

Thus far, as for $BD_3$, $eBW_3$, and $ePH_3$, estimated values for three parameters, $eBC_3$, $eBW_3$, $ePH_3$, were obtained. Here, the shape of the component band is assumed to be Gaussian. If the shape of the component band is assumed to be Lorentzian, since the bandwidth is 1.47 times as large as that of Gaussian, the component exceeding $OV_3$ appears. Therefore, the Lorentzian component band is rejected.

Figure 7:
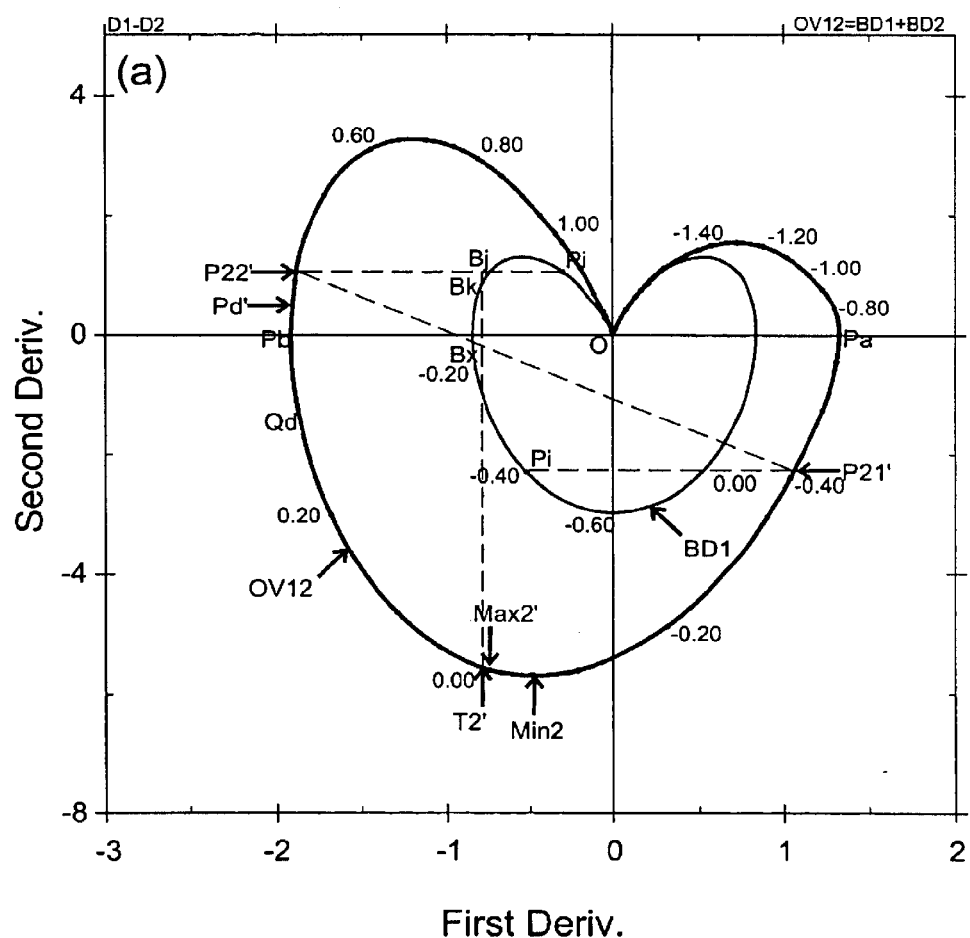
FIG. 7 is D1–D2 plots for $OV_{12}$ and $BD_1$.
Figure 8:
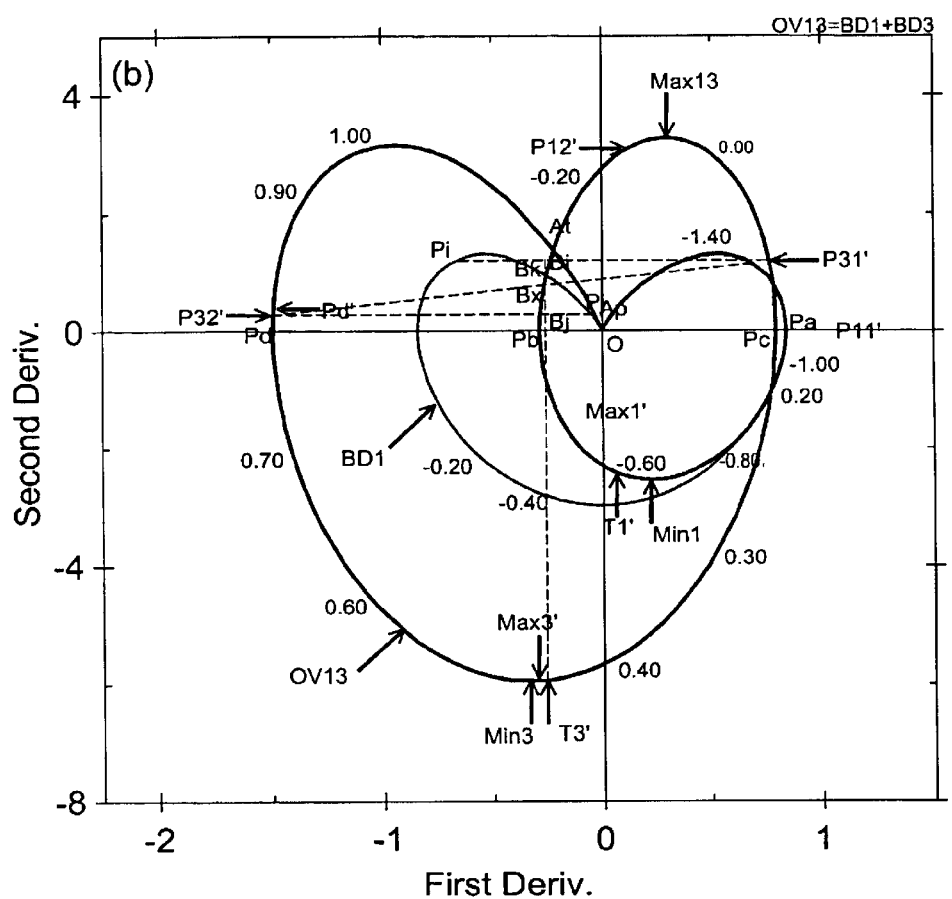
FIG. 8 is D1–D2 plots for $OV_{13}$ and $BD_1$.
Figure 9:
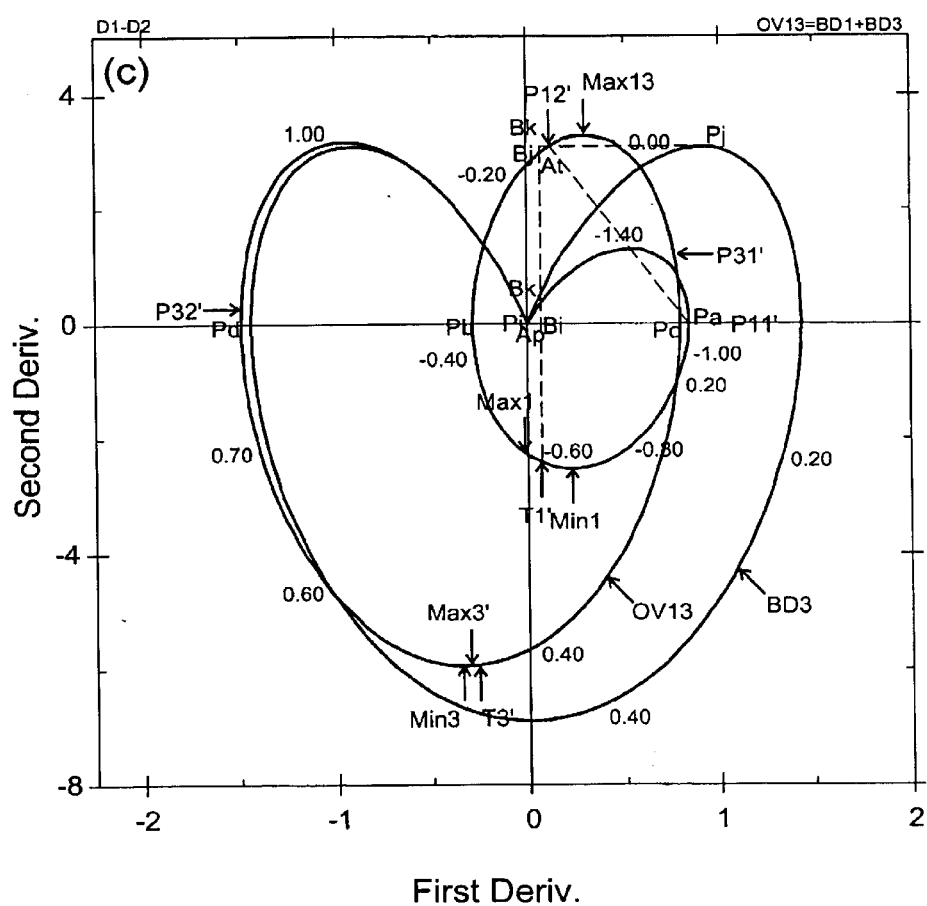
FIG. 9 is D1–D2 plots for $OV_{13}$ and $BD_3$.

After component band $BD_3$ was estimated, a band stripping operation is performed, further estimating a component band. In order to explain this procedure, as an ideal case, algebraic geometrical explanation goes. FIG. 7 shows overlaid D1–D2 plots of $OV_{12}$ (=$BD_1$+$BD_2$) wherein two component band $BD_1$ and $BD_2$ overlapped and $BD_1$. FIG. 8 shows D1–D2 plots of $OV_{13}$ (=$BD_1$+$BD_3$) wherein two component bands $BD_1$ and $BD_3$ overlapped and $BD_1$. FIG. 9 shows D1–D2 plots of $OV_{13}$ and $BD_3$.

As can be seen from FIG. 7, since Min2 and Max2' are not close to each other, it is more likely or apparent that overlap between the component bands $BD_1$ and $BD_2$ is strong.

In FIGS. 8 and 9, the local maximum Max13 indicates that the typical valley exists between $BD_3$ and $BD_1$. The appearance of the valley arises from the lower degree of overlap compared with that of $OV_{12}$. In FIG. 8, the curved portion from the origin O to Min1 via point $P_a$ substantially overlaps with the curved portion of the right half of $BD_1$. Since Min1 and Max1' are not close to each other, around the vertex of BD1, they are affected by overlap of $BD_2$ and/or $BD_3$. In FIG. 9, the curved portion from the origin O to Min3 via point $P_d$ substantially superposes on the curved portion of the left half of $BD_3$. Since Min3 and Max3' are close to each other, the band center position of $BD_3$ is in the vicinity thereof.

In FIG. 8, when estimating for $BD_3$, there is no problem when point $B_x$ is used for estimating point $B_k$. However, since there is the valley shown in FIG. 9, the curved portion of the left-hand side of $BD_1$ is greatly deformed and since line segment $P_{12}'P_{11}'$ and the perpendicular line to D1-axis passing point Ti' do not intersect, point $B_k$ exists at a position with line segment $P_{12}'P_{11}'$ extended. In addition, the curved portion from the origin O to Min 1 via point $P_a$ substantially superposes on the curved portion of the right half of $BD_1$ and point $B_k$ is in the vicinity of point $B_x$. Therefore, it is desirable to calculate the peak height from the length of line segment $T_1'B_i$.

(Step 2)

Figure 10:
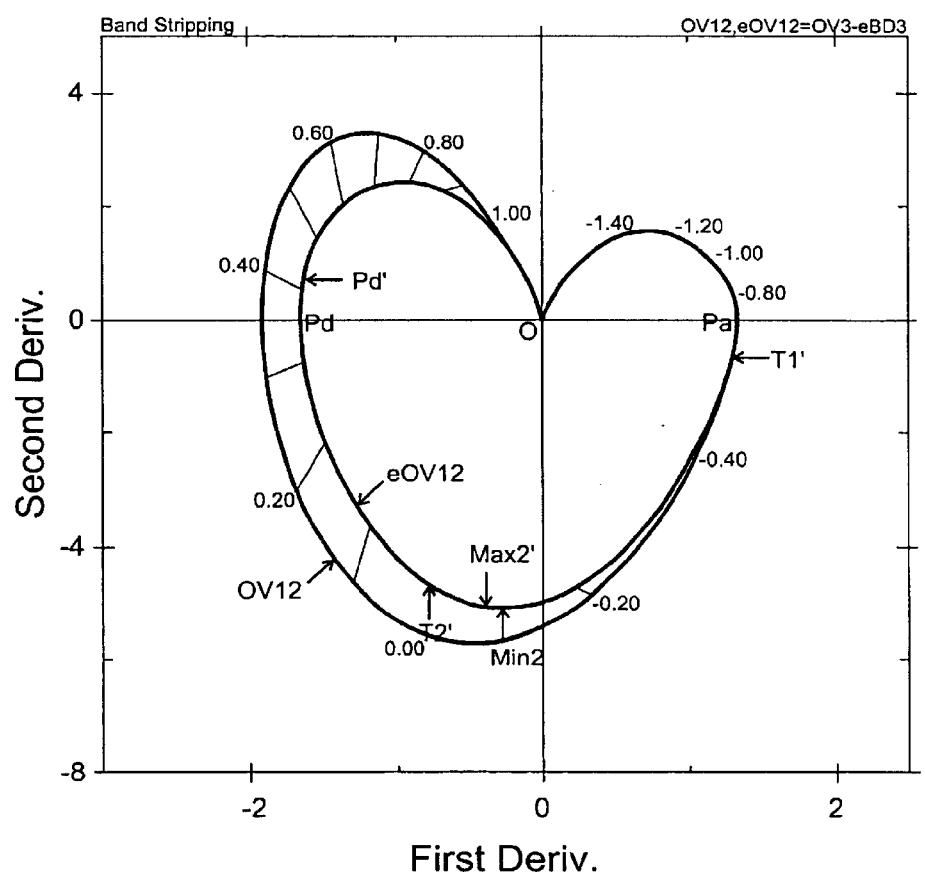
FIG. 10 is D1–D2 plots for $OV_{12}$ and $eOV_{12}$.

Now that estimated values were obtained on $BD_3$, $BD_3$ can be expressed mathematically with Equation (6). This is denoted as $eBD_3$. $eOV_{12}$ is found by band stripping $eBD_3$ from $OV_3$. That is, $eOV_{12}$=$OV_3$-$eBD_3$. In FIG. 10, D1–D2 plots are shown regarding $OV_{12}$ and $eOV_{12}$. For comparison, the iso-wavenumber lines are also drawn. Band parameter values for new component band $eBD_2$ are estimated from $eOV_{12}$.

Figure 11:
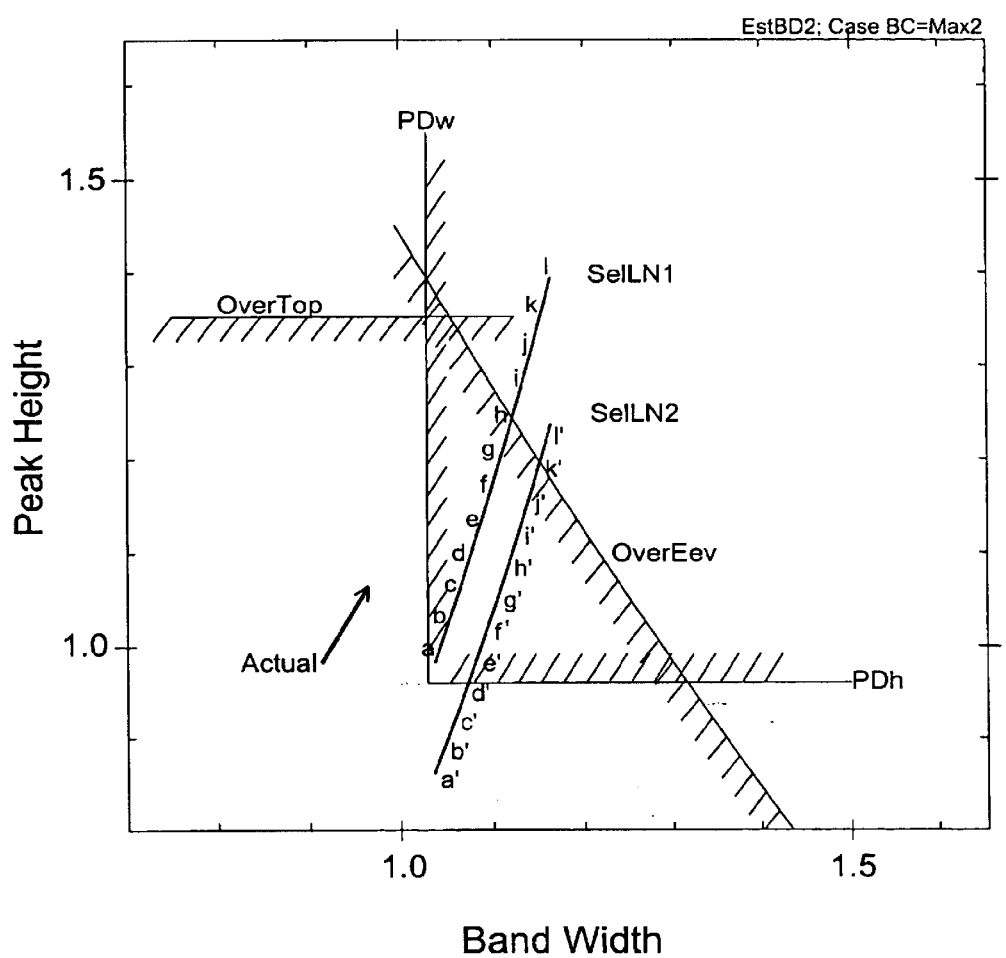
FIG. 11 is a graph showing the permissible range of the bandwidth and peak height for $BD_2$ estimation.

By the same procedure taken in Table 1 and FIG. 6, Table 2 and FIG. 11 are prepared. Estimated values for $BD_2$ are selected in the vicinity of point h' in FIG. 11. That is, $eBC_2$=-0.08, $eBW_2$=1.11, $ePH_2$=1.06. In this case, the true value for $BD_2$ indicated as 'actual' is not within the hatched triangle. This is due to the poorly estimated parameter values for $eBC_3$. However, an iterative operation described later can improve band parameter values for $eBC_3$.

TABLE 2

| Set of estimated value | X coordinate of eP22 | $eBW_2$ | $ePH2A$ | $ePH2B$ |
| --- | --- | --- | --- | --- |
| EstBD2a | 0.360 | 1.04 | 0.982 | 0.866 |
| EstBD2b | 0.365 | 1.05 | 1.02 | 0.896 |
| EstBD2c | 0.370 | 1.06 | 1.05 | 0.928 |
| EstBD2d | 0.375 | 1.07 | 1.09 | 0.96 |
| EstBD2e | 0.380 | 1.08 | 1.12 | 0.992 |
| EstBD2f | 0.385 | 1.09 | 1.16 | 1.03 |
| EstBD2g | 0.390 | 1.11 | 1.2 | 1.06 |
| EstBD2h | 0.395 | 1.12 | 1.23 | 1.09 |
| EstBD2i | 0.400 | 1.13 | 1.27 | 1.13 |
| EstBD2j | 0.405 | 1.14 | 1.31 | 1.16 |
| EstBD2k | 0.410 | 1.15 | 1.35 | 1.2 |
| EstBD2l | 0.415 | 1.17 | 1.39 | 1.24 |
| EstBD2m | 0.420 | 1.18 | 1.43 | 1.27 |
| EstBD2n | 0.425 | 1.19 | 1.47 | 1.31 |

(Step3)

Figure 12:
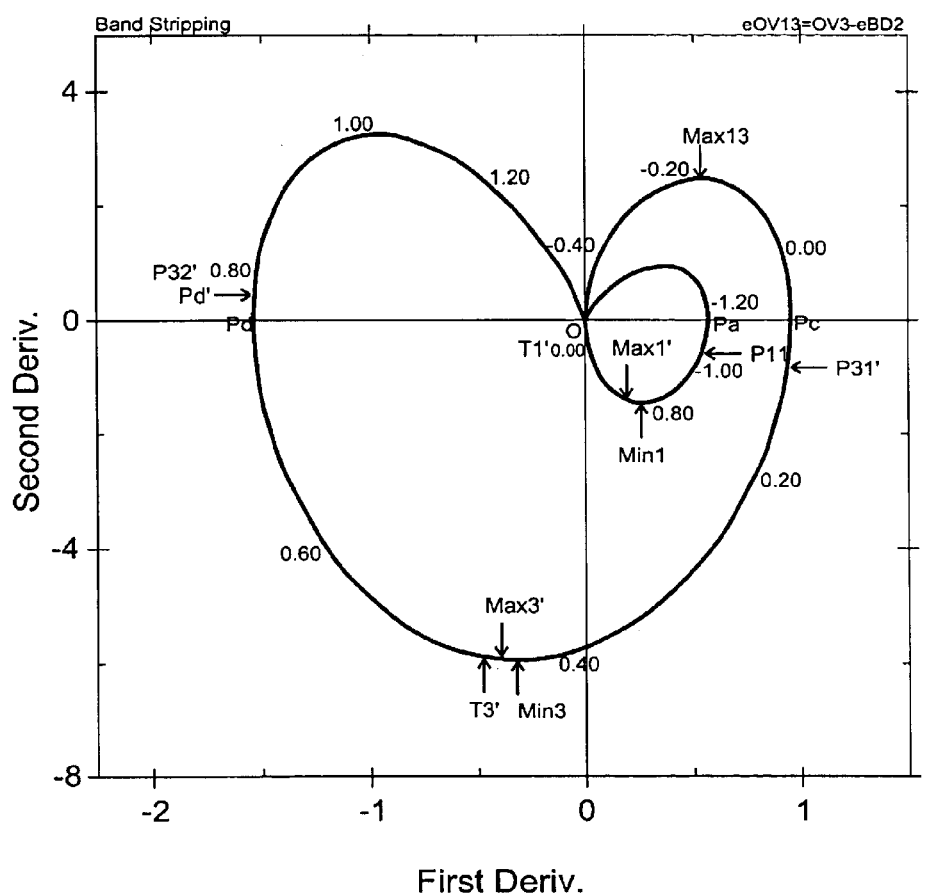
FIG. 12 is D1–D2 plots for $eOV_{13}$.

$eOV_{13}$ is found by band stripping $eBD_2$ from $OV_3$. D1–D2 plots regarding $eOV_{13}$ are shown in FIG. 12. As is clear from FIG. 12, since two local minima appear, it is found that there are at least three component bands within $OV_3$ and the band center position could be estimated. Here, local minima Min1 and Min 3 indicate the existence of corresponding component bands $BD_1$ and $BD_3$, respectively.

When the positions of Max 1' and Max 3' corresponding to Min 1 ($X_{min1}$=-0.8257) and Min 3 ($X_{min3}$=0.4276), respectively, are calculated, $X_{max1}$=-0.7757 and $X_{max3}$= 0.4403. Min 3 and Max 3' found here are closer to the true value T3' compared to Min 3 and Max 3' in FIG. 4 or 5. This is due to band stripping effect, which has reduced overlapping effect between component bands.

Figure 13:
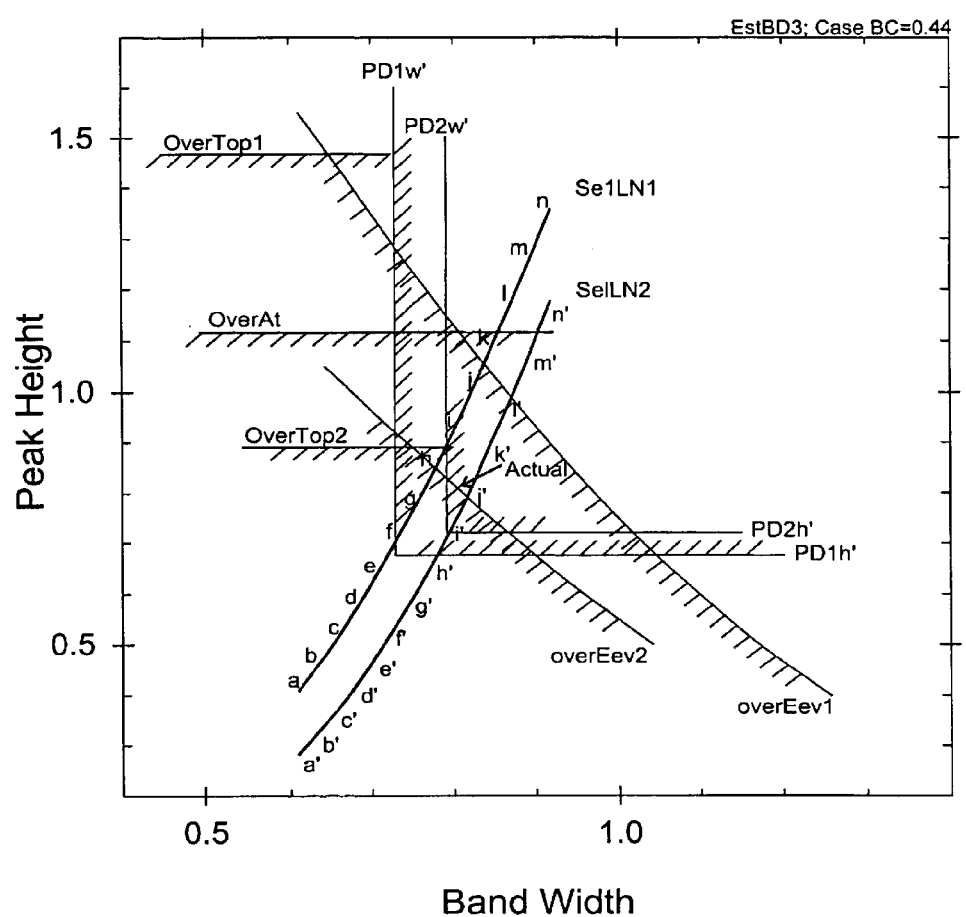
FIG. 13 is a graph showing the permissible range of the bandwidth and peak height for $BD_3$ estimation.

Therefore, $eBC_3$ in Step 1 is replaced by $X_{max3}$ just obtained, and a set of $eBD_3$ and its constraint conditions are recalculated in the same manner as in Step 1. At the same time, constraint conditions are also calculated from FIG. 12. The set of $eBD_3$ obtained by this and the constraint conditions are shown in Table 3 and FIG. 13. According to the results, constraint conditions subjected to them are the narrower permissible regions. The intermediate point of points i' and j' on SelLN2 is selected as a new estimated point. That is, $eBC_3$=0.44, $eBW_3$=0.81, and $ePH_3$=0.78.

TABLE 3

| Set of estimated value | X coordinate of eP32 | $eBW_3$ | $ePH3A$ | $ePH3B$ |
| --- | --- | --- | --- | --- |
| EstBD3a | 0.70 | 0.612 | 0.409 | 0.284 |
| EstBD3b | 0.71 | 0.636 | 0.46 | 0.326 |
| EstBD3c | 0.72 | 0.659 | 0.515 | 0.372 |
| EstBD3d | 0.73 | 0.683 | 0.574 | 0.422 |
| EstBD3e | 0.74 | 0.706 | 0.636 | 0.476 |
| EstBD3f | 0.75 | 0.730 | 0.702 | 0.535 |
| EstBD3g | 0.76 | 0.753 | 0.772 | 0.598 |
| EstBD3h | 0.77 | 0.777 | 0.846 | 0.666 |
| EstBD3i | 0.78 | 0.801 | 0.923 | 0.739 |
| EstBD3j | 0.79 | 0.824 | 1.0 | 0.816 |
| EstBD3k | 0.80 | 0.848 | 1.09 | 0.899 |
| EstBD3l | 0.81 | 0.871 | 1.17 | 0.986 |
| EstBD3m | 0.82 | 0.895 | 1.26 | 1.08 |
| EstBD3n | 0.83 | 0.918 | 1.36 | 1.18 |

(Step4)

When the band parameter values for $BD_2$ are estimated in the same procedure as in the Step 2, $eBC_2$=-0.03, $eBW_2$=1.04, and $ePH_2$=1.01.

When compared with the result of the Step 2, the suitability is improved.

(Step5)

Further, by iterating the same procedure as in the Step3, a new set of estimated values for $BD_3$ is obtained. That is, $eBC_3=0.449$, $eBW_3=0.814$, and $ePH_3=0.800$.

(Step6)

Further, band parameter values for $BD_2$ are estimated and $eBC_2=-0.02$, $eBW_2=1.04$, and $ePH_2=0.967$. Judging that estimated values are no longer improved with the iterative operation, the operation is hereby suspended.

(Step7)

Figure 14:
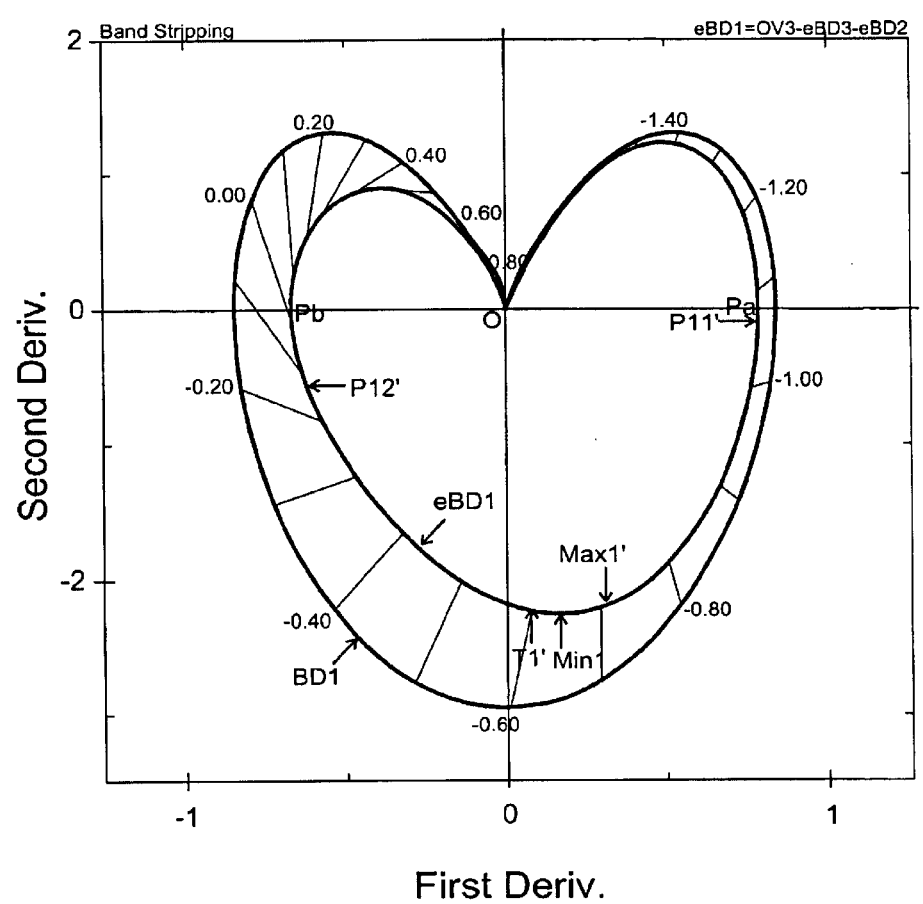
FIG. 14 is D1–D2 plots for $BD_1$ and $eBD1$.

Finally, band parameter values for $BD_1$ are estimated. This can be found by the geometry illustrated in FIG. 9. That is, $eBC_1=-0.642$, $eBW_1=1.15$, and $ePH_1=0.512$. In addition, when the suitability of estimated parameter values for $BD_2$ and $BD_3$ is good, by D1–D2 plots where $eBD_1=OV_3-eBD_2-eBD_3$, the band parameter values for $eBD_1$ can also be estimated. In FIG. 14, D1–D2 plots of $eBD_1$ and $BD_1$ are shown, whose shape is asymmetric and the curved portion of the left-hand side is smaller.

These results show that estimated values of $eBD_2$ or $eBD_3$ are not good. Although the existence of the fourth component band cannot be denied, it cannot be judged from the estimated values obtained so far. Therefore, complementary matching is conducted assuming that there are three component bands.

For confirmation, the estimated values at this stage are as follows:

Estimated component band $eBD_1$:
$eBC_1=-0.642$
$eBW_1=1.15$
$ePH_1=0.512$
Estimated component band $eBD_2$:
$eBC_2=0.002$
$eBW_2=1.01$
$ePH_2=0.967$
Estimated component band $eBD_3$:
$eBC_3=0.449$
$eBW_3=0.814$
$ePH_3=0.800$ (Complementary Matching)

Figure 15:
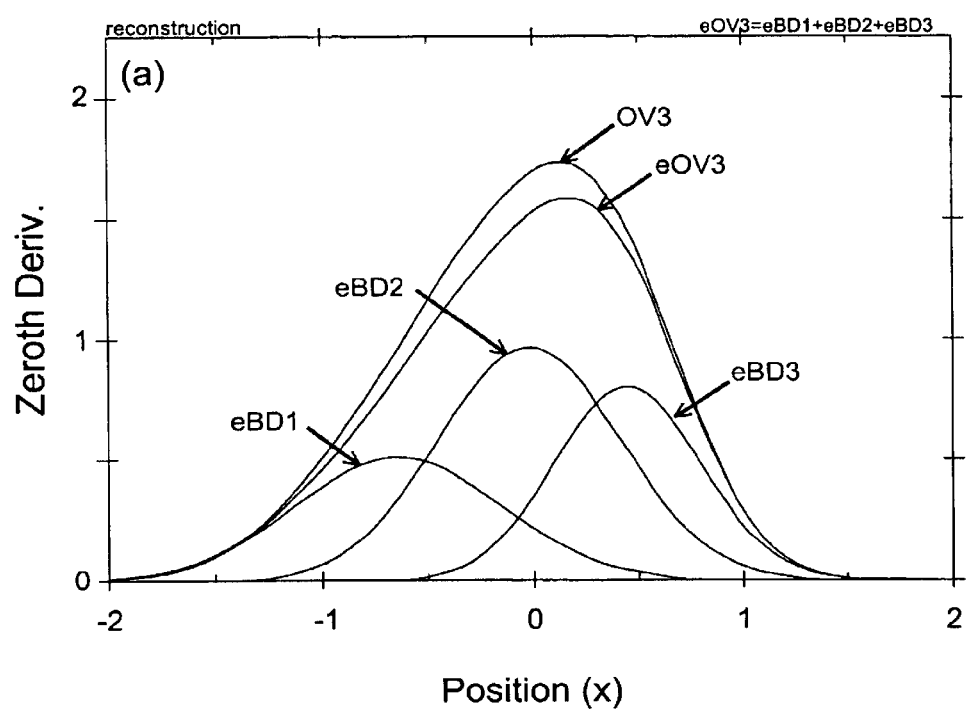
FIG. 15 is a graph depicting spectral profile of $eBD_1$, $eBD_2$, $eBD_3$, $eOV_3$, and $OV_3$.
Figure 16:
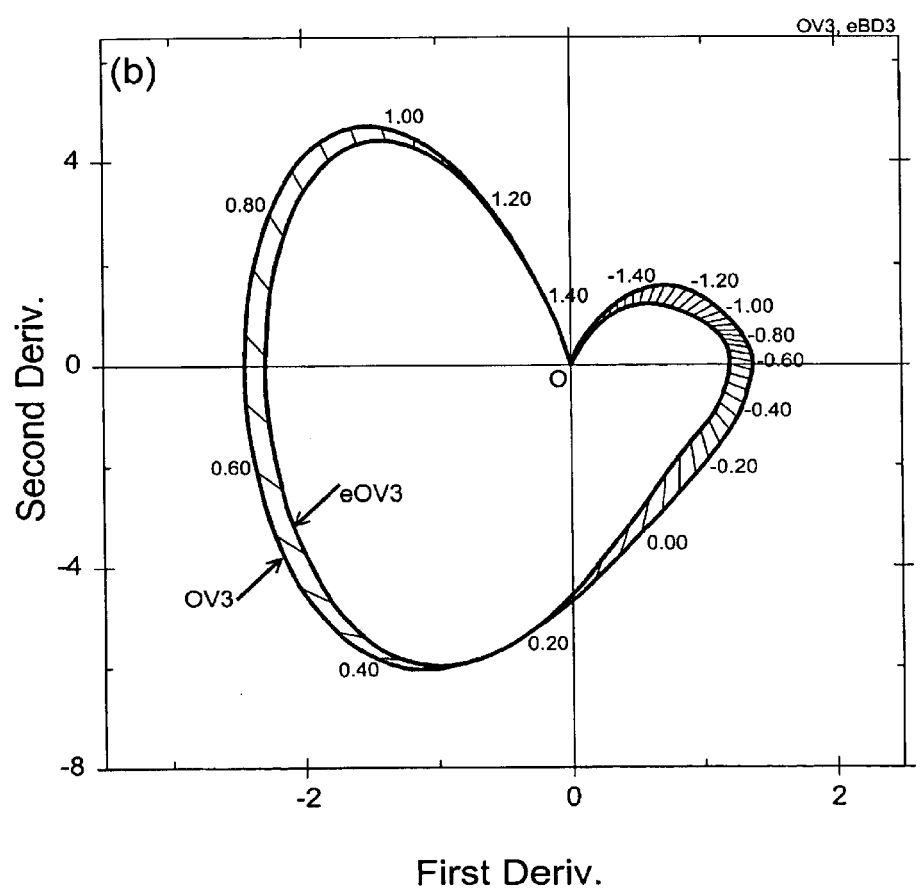
FIG. 16 is D1–D2 plots for $eOV_3$ and $OV_3$.

The suitability of the component bands estimated at the present stage is examined. In FIG. 15, $eBD_1$ $eBD_2$ $eBD_3$ and $eOV_3$ are shown together with $OV_3$. In FIG. 16, D1–D2 plots of $eOV_3$ and $OV_3$ are shown. In the figures, the iso-wavenumber lines between $OV_3$ and $eOV_3$ were also drawn and the profiles of $eOV_3$ and $OV_3$ are not coincident. However, since it is hard to examine from FIG. 15 or 16 which component band has good or poor suitability for an estimation, the improvement of band parameter values should be performed and evaluated according to other criteria.

Therefore, with a complementary estimated component band, the improvement of band parameter, values is achieved. Here, a complementary estimated component band is the component band subtracting all the other component bands except only one component band between estimated component bands from the spectrum. That is, the complementary estimated component band $cBD_3$ with respect to $BD_3$ is represented as $cBD_3=OV_3-eBD_1-eBD_2$. If estimated values of all the band parameters are coincident with the true values, $eBD_3$ and $cBD_3$ are also coincident. Likewise, the complementary estimated component band $cBD_2$ or $cBD_1$ can be calculated.

Figure 17:
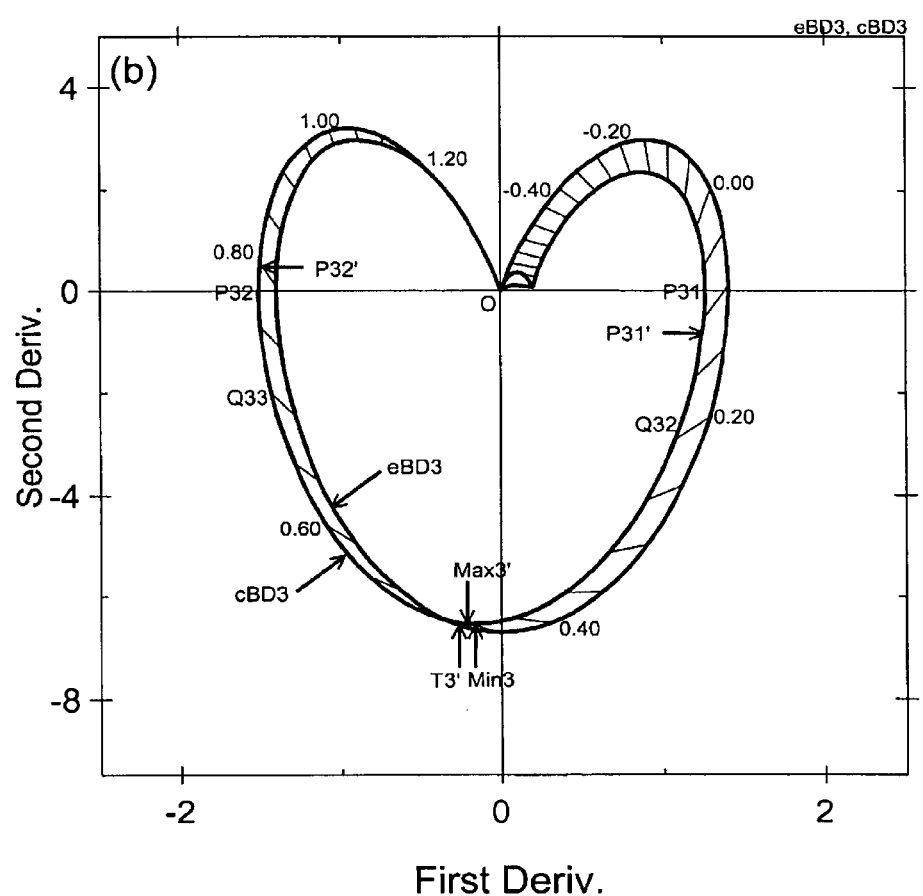
FIG. 17 is D1–D2 plots for $eBD_3$ and $cBD_3$.
Figure 18:
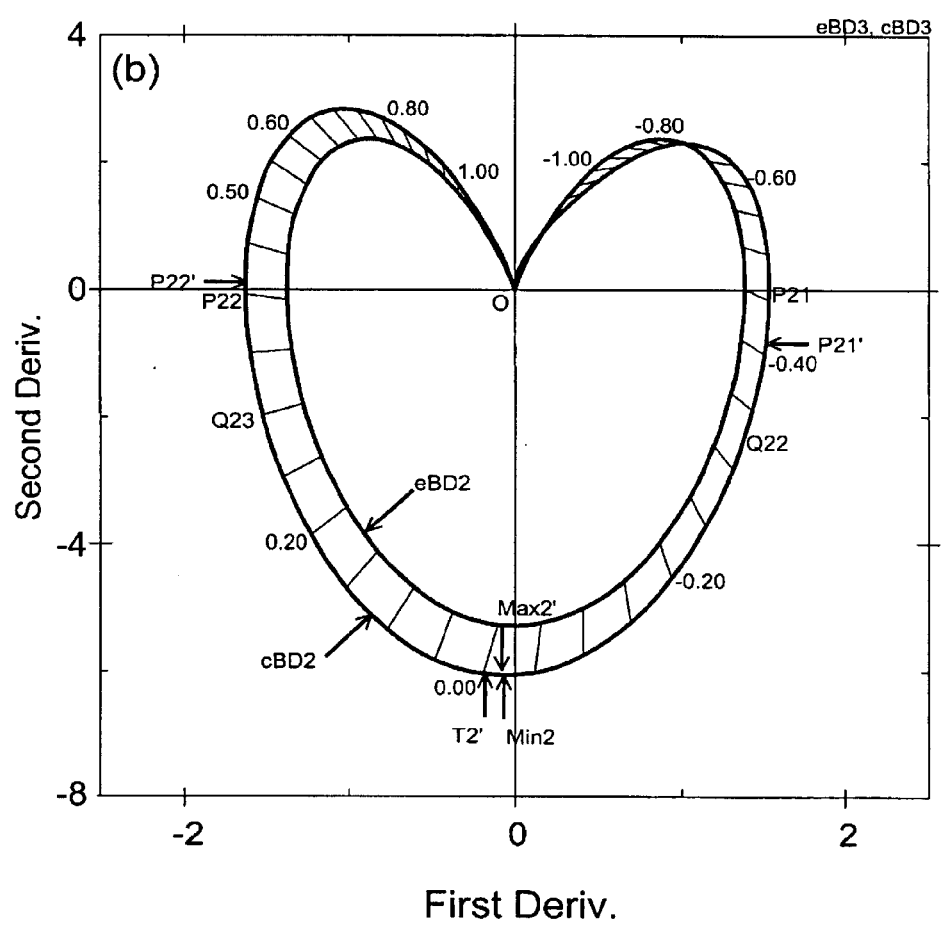
FIG. 18 is D1–D2 plots for $eBD_2$ and $cBD_2$.
Figure 19:
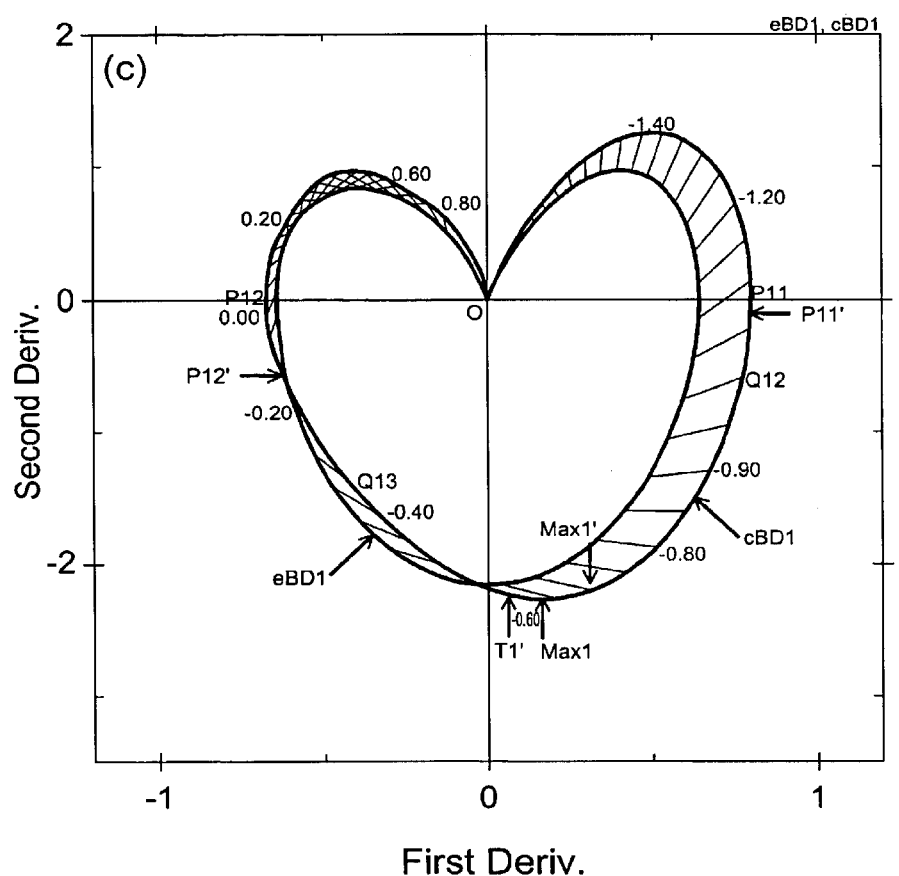
FIG. 19 is D1–D2 plots for $eBD_1$ and $cBD_1$.

FIG. 17 shows D1–D2 plots of $eBD_3$ and $cBD_3$. Likewise, FIGS. 18 and 19 show D1–D2 plots of $eBD_2$ and $cBD_2$, and $eBD_1$ and $cBD_1$, respectively. In FIG. 17, since Min3 ($X_{min3}=0.4363$), the characteristic point of $cBD_3$, is close to Max3' ($X_{max3}=0.4465$), the band center position may be estimated at the corresponding local maximum or minimum value of $eBD_3$. The right-hand side of the plot is smaller compared with $eBD_3$. This may be because $eBD_2$ or $eBD_3$ is estimated smaller than the true value.

Next, in FIG. 18, $eBD_2$ is examined. Since Min2 ($X_{min2}=-0.0195$), the characteristic point of $cBD_2$, is close to Max2' ($X_{max2}=-0.0152$), the band center position of $BD_2$ may be estimated at the corresponding local maximum or minimum value of $eBD_2$. The plot of a single band is heart-shaped since the peak height $ePH_2$ is estimated smaller than the true value.

Further, in FIG. 19, $eBD_1$ is examined. Min1 ($X_{min1}=-0.6390$), the characteristic point of $cBD_1$, and Max1' ($X_{max1}=-0.7038$) are not close to each other. In addition, since the degree of the symmetry of the shape of $cBD_1$ is not good, the estimated values for the band parameters are not good.

Now that suitability of an estimation of each component band was made clear, suitability is enhanced by adjusting each band parameter value. As the criteria for suitability of an evaluation value, SumLS, the total sum of the distances of the iso-wavenumber lines between $OV_3$ and $eOV_3$ on D1–D2 plots is provided and by adjusting each parameter value so as to make the evaluation value small, suitability is enhanced.

As examined from the profiles of FIGS. 17 to 19, first, parameter values for $eBD_1$ are adjusted. Adjustment is performed in the order of $eBD_1$, $eBW_1$, and $ePH_1$. New $eBC_1$ is determined as the estimated value when SumLS is the minimum by changing it in the vicinity of the current $eBC_1$. When SumLS is calculated and eBCi is adjusted regarding the total range of X ($-2 \leq X \leq 2$), $eBC_1=-0.576$. When SumLS is calculated and $eBC_1$ is adjusted within the limited range of the inflection points $P_{11}$ to $P_{12}$, $eBC_1=-0.594$. Further, when SumLS is calculated and $eBC_1$ is adjusted within the limited range of the secondary inflection points $Q_{12}$ to $Q_{13}$, $eBC_1=-0.600$. Since the true value of $BC_1$ is $-0.5978$, at the early stage of the optimization of band center position, that is, at the stage where suitability of the estimation is poor, it is better to estimate the band center position limiting to the vicinity of a corresponding local maximum or minimum to calculate SumLS and adjust the parameters.

Likewise, as for estimating $eBW_1$, adjustment is performed. As for estimating $ePH_1$, it is better to find such $ePH_1$ as making SumLS minimum regarding the entire ranges of X.

Figure 20:
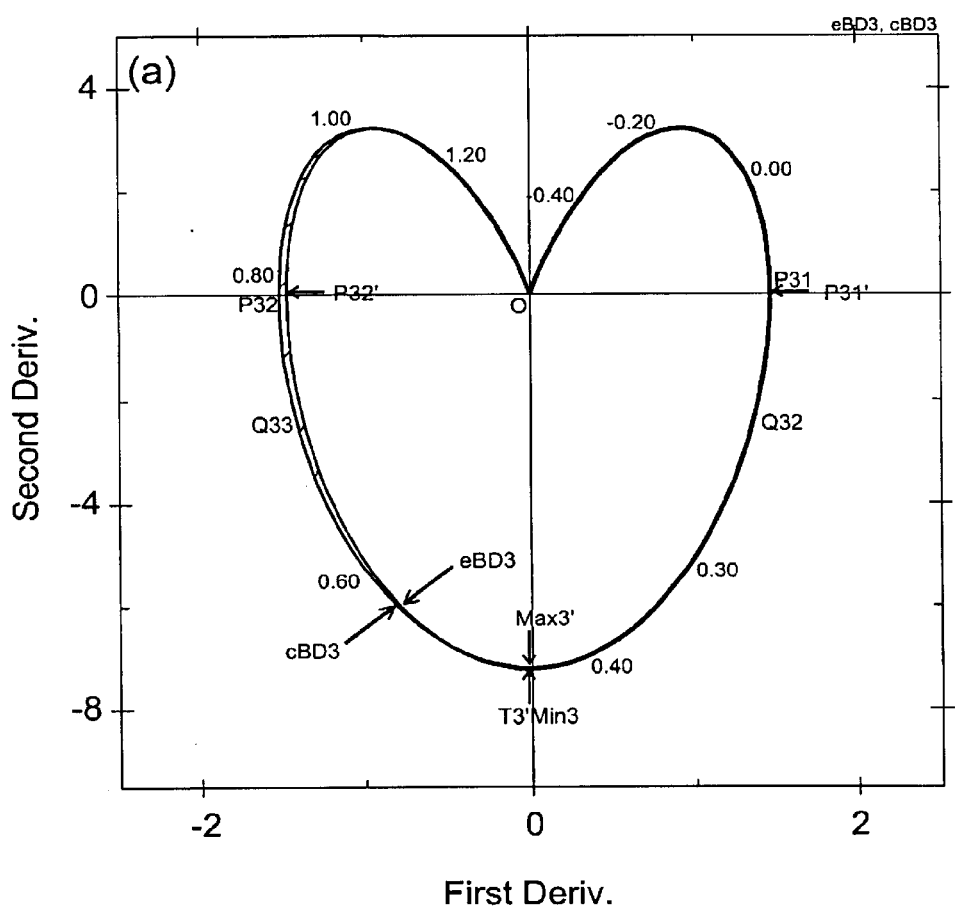
FIG. 20 is D1–D2 plots for $eBD_3$ and $cBD_3$ after the parameter values are improved by SumLS.
Figure 21:
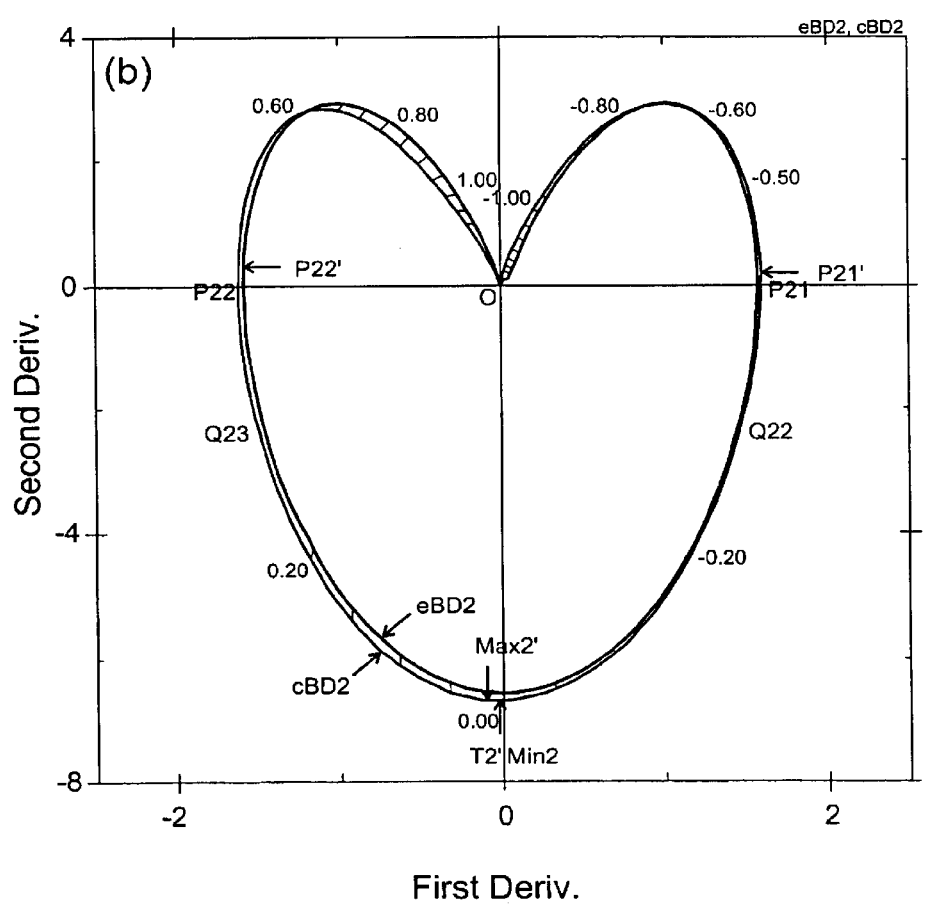
FIG. 21 is D1–D2 plots for $eBD_2$ and $cBD_2$ after the parameter values are improved by SumLS.
Figure 22:
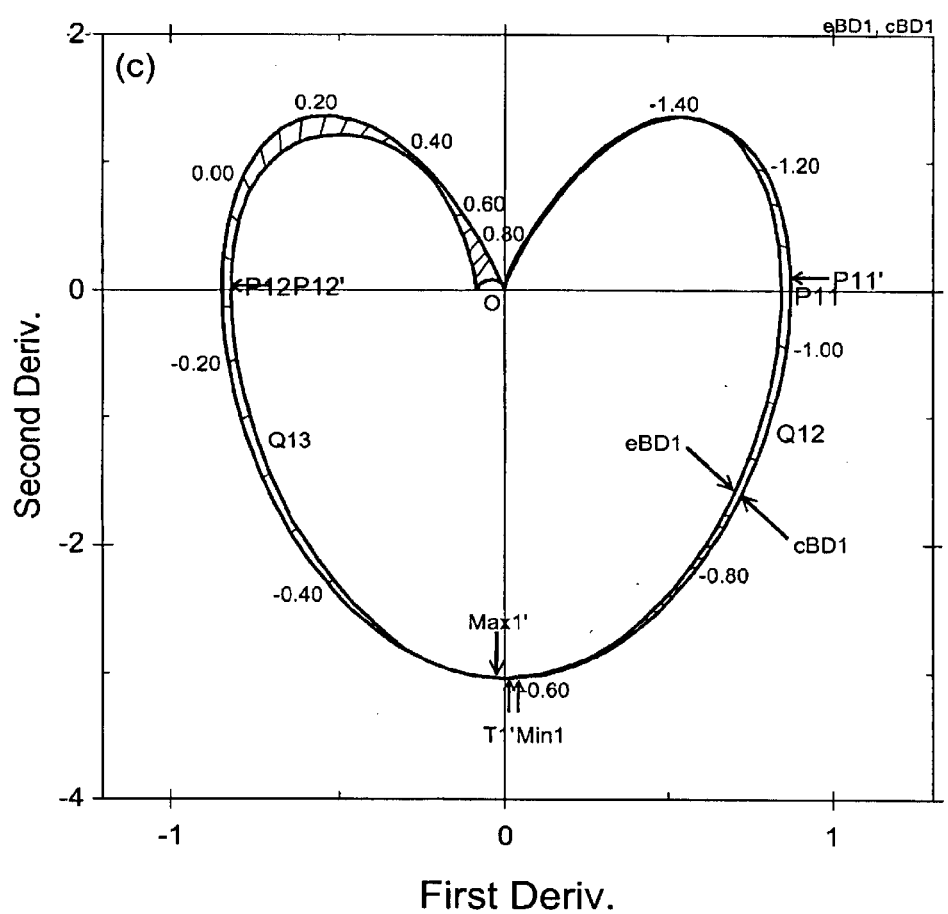
FIG. 22 is D1–D2 plots for $eBD_1$ and $cBD_1$ after the parameter values are improved by SumLS.

The same kind of operation is conducted on $eBD_2$ and $eBD_3$ as well. FIGS. 20 to 22 show D1–D2 plots of the complementary estimated component band after iterating a series of the parameter values adjustment three times. Compared FIGS. 17 to 19, suitability of the band parameter values is improved.

The optimization of all the band parameter values cannot be simultaneously achieved when the estimated value of each band parameter values is adjusted alone. The optimization of the estimated values for $eBD_1$ are so adjusted as to enhance the degree of coincidence between $eBD_1$ and $cBD_1$ as well as to improve the symmetry of $cBD_2$ which is the adjacent complementary estimated component band in FIG. 18.

Here, the criteria of symmetry are so defined that two inflection points are symmetrical to the Y-axis. That is, for example, the parameter values are so adjusted that the length of the line segment $OP_{11}$ is equal to that of the line segment $OP_{12}$.

For example, in adjusting $ePH_1$, $ePH_{11}$ where SumLS is the minimum ($ePH_{11}$=0.646) is found. Next, $ePH_{1j}$ is found where the length of line segment $OP_{11}$ is equal to that of line segment $OP_{12}$. Then its mean value ($ePH_{1i+}$ $ePH_{1j}$)/2 is selected as an optimum estimated value. The reason for selecting the mean value is that the symmetry of $cBD_2$ is affected from the band of both sides. By such iterated operations, $ePH_{1i}$ and $ePH_{1j}$ become coincident.

Figure 23:
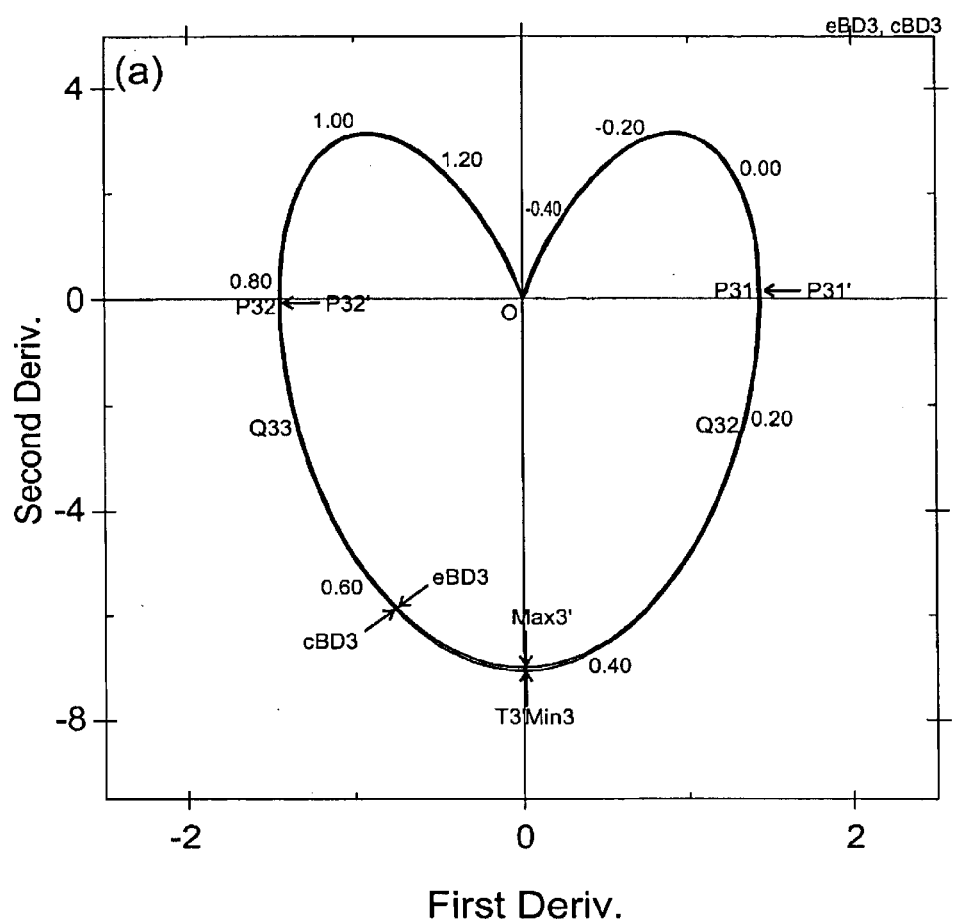
FIG. 23 is D1–D2 plots for $eBD_3$ and $cBD_3$ after the parameter values are improved in coincidence and symmetry.
Figure 24:
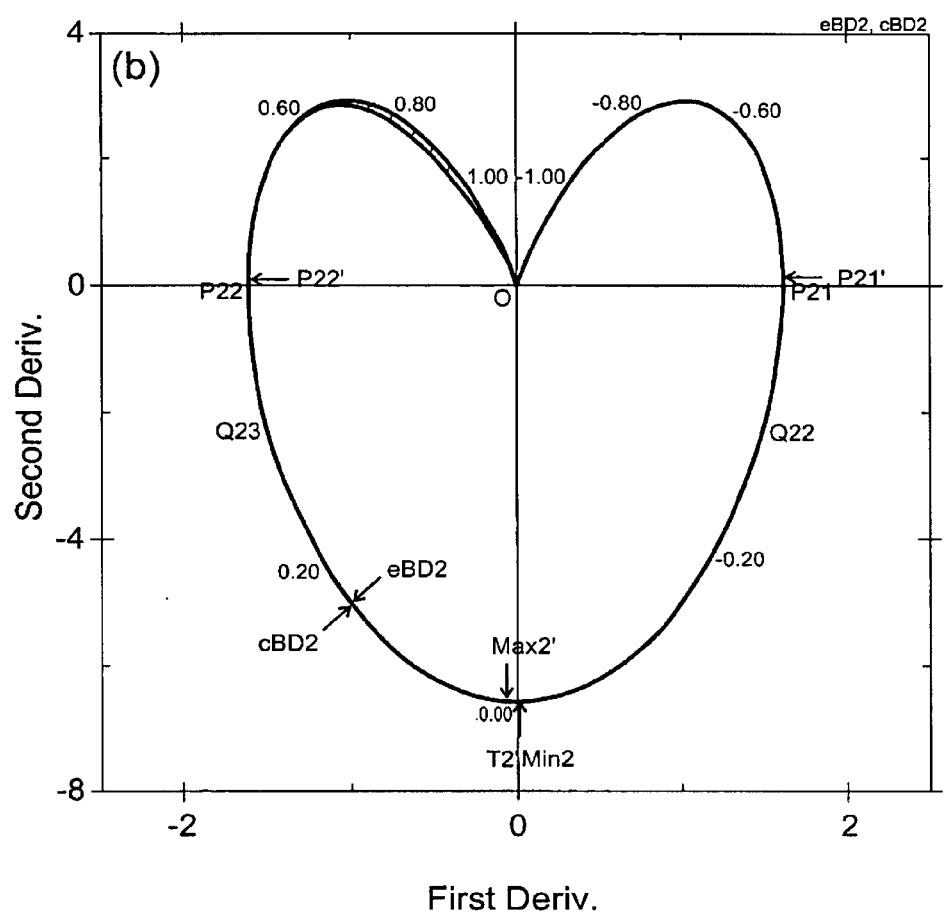
FIG. 24 is D1–D2 plots for $eBD_2$ and $cBD_2$ after the parameter values are improved in coincidence and symmetry.
Figure 25:
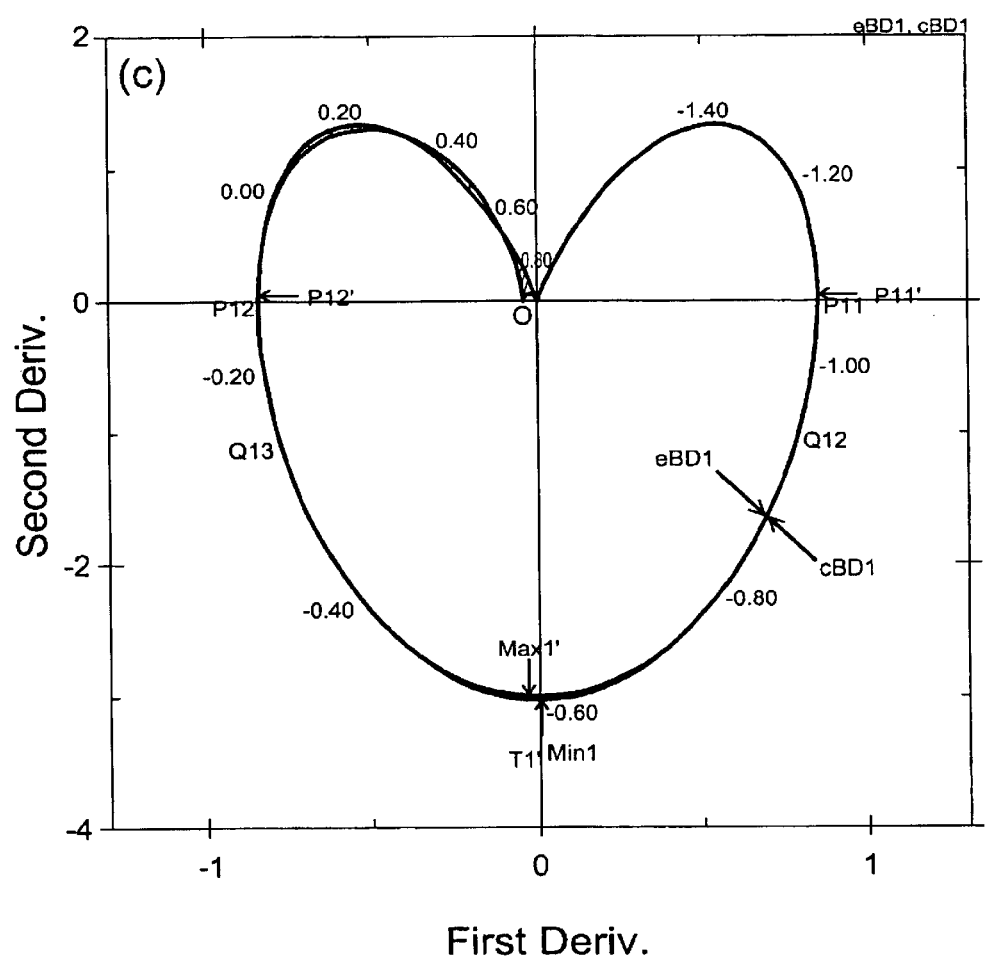
FIG. 25 is D1–D2 plots for $eBD_1$ and $cBD_1$ after the parameter values are improved in coincidence and symmetry.

In adjusting the band center position $eBC_1$, the above operation is not always required since the good estimated value is obtained for $eBC_1$ where SumLS has the minimum value. Likewise, the improvement of the coincidence between $eBD_2$ and $cBD_2$ and in the symmetry of $cBD_2$ is achieved. The results are shown in FIGS. 23 to 25. Finally, the good results were obtained as follows:

Estimated component band $eBD_1$:
  $eBC_1$=−0.597
  $eBW_1$=1.094
  $ePH_1$=0.648
Estimated component band $eBD_2$:
  $eBC_2$=0.004
  $eBW_2$=0.952
  $ePH_2$=1.070
Estimated component band $eBD_3$:
  $eBC_3$=0.456
  $eBW_3$=0.794
  $ePH_3$=0.800

Finally, the examination of the existence of the hidden component bands or the evaluation of the residual component rBD is performed. rBD is represented as $rBD=OV_3-eBD_1-eBD_2-eBD_3$. Virtual component band vBD whose parameter values are already known is introduced and D1–D2 plots of the data with rBD, remaining component bands, and vBD added are evaluated. Since the derivative plot of vBD is already known, it can be evaluated by the shape of the overlapping residual component. In addition, an evaluation of a complementary estimated component band is also made. Thus, when a hidden component band can be estimated, it is a good way to return to the first step, finding the estimated value of parameter values for a new component band from constraint conditions, thereby improving the parameter values of the said component band by the similar method.

The estimation method of the present invention was described above by using the simulation data. In estimating actually measured data, it is necessary to differentiate digitally in order to obtain derivatives plots. Therefore, in the case where the band to be measured is sharp, it is necessary to measure with the small data interval for measurement.

Particularly, in the present invention, as for the analyzed object, what matters is a method of analyzing the obtained data and in order to obtain the data, the conventional spectrophotometer can be used as it is thereby requiring no new spectrophotometer. The component bands can be estimated from the spectral data of the analyzed object by outputting spectral information, thereafter putting into a data station or a computer with programs developed based on the proposed method. These programs can be installed into the spectrophotometer.

(Effect of the Invention)

When the procedure of the spectral analysis method of the present invention is used, several component bands can be easily estimated as for the analyzed object having a spectral profile which contains several component bands.

Summary on the procedure of the spectral analysis described above is as follows:

(1) The band center position of corresponding component band is determined noting the typical local minimum, and/or local maximum of the two-dimensional derivative plot (including D1–D2 plots) of the spectra of the analyzed object.

(2) The candidates for the bandwidth values are determined by selecting candidates of several points in the vicinity of zero-crossing points of the second derivatives, estimating the bandwidth of the corresponding component band from the candidates of inflection points, and estimating the peak height of the corresponding component band from the algebraic geometrical condition of two-dimensional derivative plot. Further, band parameter values are imposed by the constraint conditions and the estimated value is determined.

(3) The band parameter values are estimated by finding the component bands in order by band stripping.

(4) The estimated band parameter values are optimized and improved by using the complementary matching method and considering the overlapping effects among component bands.

(5) The band parameter values for component bands are determined among best fitting band shape since the profile of each component band must be line symmetry when each component band is extracted.

(6) Suitability of the band shape and existence of hidden bands are examined by observing profile of each component band after optimization of the band parameter values.

Description of the preferred embodiment described herein is illustrative and not restrictive, the scope of the invention being indicated by the appended claims and all variations which come within the meaning of the claims are intended to be embraced therein.

What is claimed is:

1. A method of spectrum analysis in two-dimensional representations of a specific analyzed object, wherein spectral data containing the intensity of the signal output from a spectrophotometer is represented as a function of wave-number, wavelength or time, the n-th and m-th derivatives of spectral data with respect to wave-number, wavelength or time are calculated, where n and m are integers and n does not equal m, points are plotted in a two-dimensional coordinate plane such as in a X-Y coordinate system, where the X-coordinate is the n-th derivative and the Y-coordinate is the m-th derivative; characteristic information on the spectral data is obtained based on the said two-dimensional derivative plot comprising;

(A) a step wherein based on the said characteristic information, at least one component band is estimated after the band parameter values regarding at least one component band among the component bands contained in the spectral profile of the analyzed object are estimated, (B) a step wherein the two-dimensional derivative plot with a specific component band removed is obtained by clearing a specific component band or specific component bands already estimated or the two-dimensional derivative plot from th spectral profile or a two-dimensional derivative plot of the analyzed object, (C) a step wherein specific characteristic information based on the two-dimensional derivative plot with this specific component removed is obtained, and band parameter values on remaining component bands are estimated based on the said characteristic information, and (D) a step wherein the already estimated band parameter vales are so adjusted that the already estimated specific component band and the complementary estimation component band with the estimated component band removed coincide with each other, the complementary estimation component band retaining the said estimated specific component band from a spectral profile or two-dimensional derivative plot of the analyzed object;

and after estimating the component band which comprises a spectral profile of the analyzed object by estimating component bands in order by iterating steps (A) to (C), adjusting the already estimated parameter values by a step (D).

2. A method of spectrum analysis in two-dimensional representation as set forth in claim 1, wherein the component band is a Gaussian band, a Lorentzian band, or a mixture thereof.

3. A method of spectrum analysis in two-dimensional representation as set forth in claim 1, wherein n is 1 and/or 3 and m is n+1.

4. A method of spectrum analysis in two-dimensional representation as set forth in claim 2, wherein in the two-dimensional derivative plot where pairs of the first and second derivatives are represented in X-Y coordinate system, when a typical local minimum indicates the existence of a corresponding component band, an X position of the said local minimum is a first approximation of band center position Act of the said component band, setting several points on the said two-dimensional derivative plot in the vicinity of $P_d$, point of intersection of the said two-dimensional derivative plot with the X-axis, as candidates for the inflation point of the said component band, estimating the bandwidth of the said component band from the candidate of the said inflection point by the following Equation (1), estimating the peak height of the said component band from the distances between the said local minimum and the point(s) of intersection of vertical line passing through the said local minimum and the horizontal line(s) passing through the said candidate points, obtaining the candidates for band parameter values of the said component band, and further obtaining the constraint conditions subjected to the band parameter values for the said component band from the said two-dimensional derivative plot, the relation between the bandwidth $b_w$ and the X-position of the inflection point $X_p$, of a single band can be preferably expressed by $$b_w = (1/K_P) |X_c - X_P|$$

(In equation, $b_W$ is an estimated value of the bandwidth of a Gaussian or a Lorentzian band, where the coefficient $K_P$ is 0.42466 for Gaussian and 0.288675 for Lorentzian.)

5. A method of spectrum analysis in two-dimensional representation as set forth in claim 2, wherein in the two-dimensional derivative plot where pairs of the third and fourth derivatives are represented in X-Y coordinate system, when a typical local maximum indicates the existence of a corresponding component band, an X position of the said local maximum is a first approximation of band center position Act of the said component band, setting several points on the said two-dimensional derivative plot in the vicinity of $Q_d$, point of intersection of the said two-dimensional derivative plot with the X-axis, as candidates for the secondary inflection point of the said component band, estimating the bandwidth of the said component band from the candidate of the said secondary inflection point by the following Equation (2), estimating the peak height of the said component band from the distances between the said local maximum and the point(s) of intersection of vertical line passing through the said local maximum and the horizontal line(s) passing through the said candidate points, obtaining the candidates for band parameter values of the said component band from the said two-dimensional derivative plot, the relation between the bandwidth $b_w$ and the X-position of the secondary inflection point $X_Q$ of a single band can be preferably expressed by $$b_w = (1/K_P) |X_c - X_Q|$$

(In the equation, $b_W$ is an estimated value of the bandwidth of a Gaussian or a Lorentzian band, where the coefficient $K_Q$ is 0.31508 for Gaussian and 0.16426 for Lorentzian.)

6. A method of spectrum analysis in two-dimensional representation as set forth in claim 1, wherein spectral data are infrared spectra, visible light spectra, ultraviolet spectra, Raman spectra, X-ray diffractograms, and chromatograms.

* * * * *